(12) United States Patent
Roe et al.

(10) Patent No.: US 7,806,880 B2
(45) Date of Patent: Oct. 5, 2010

(54) PULL-ON WEARABLE ARTICLE WITH INFORMATIONAL IMAGE

(75) Inventors: Donald Carroll Roe, West Chester Twp., OH (US); Melanie D. Allen, Newport, KY (US); Kathleen Quinlan Ames-Ooten, Cincinnati, OH (US); Mark John Ciesko, Cincinnati, OH (US); Barry Robert Feist, Madeira, OH (US); Eiro Fukuda, Mason, OH (US); George Bartol Glackin, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 269 days.

(21) Appl. No.: 11/083,607

(22) Filed: Mar. 18, 2005

(65) Prior Publication Data

US 2006/0212018 A1      Sep. 21, 2006

(51) Int. Cl.
*A61F 13/15* (2006.01)

(52) U.S. Cl. .............. 604/385.01; 604/385.3; 604/387; 604/394; 604/385.24; 604/389; 604/391; 604/396

(58) Field of Classification Search ............ 604/385.01, 604/385.3, 387, 394, 385.24, 389, 391, 396
See application file for complete search history.

(56) References Cited

U.S. PATENT DOCUMENTS 2,075,189 A      3/1937   Galligan et al.
3,675,654 A      7/1972   Baker
3,759,261 A  *   9/1973   Wang .................. 604/361
3,848,594 A     11/1974   Buell
3,860,003 A      1/1975   Buell
4,022,211 A      5/1977   Timmons (Continued)

FOREIGN PATENT DOCUMENTS

DE       G 93 17 680.5        4/1995

(Continued)

OTHER PUBLICATIONS

PCT Search Report mailed Aug. 23, 2006 4 pages.

(Continued)

*Primary Examiner*—Jacqueline F. Stephens
(74) *Attorney, Agent, or Firm*—Amy M. Foust; Richard L. Alexander; Eric T. Addington

(57) ABSTRACT

A pull-on wearable article includes a main portion with an outer cover, the main portion defining a front waist region, a rear waist region, and a crotch region extending between and connecting the front and rear waist regions. First and second extendable side panels extend between and connect the main portion front waist region and the main portion rear waist region to form the article in a closed waist configuration, wherein at least a portion of each side panel is extendable between a relaxed state and an extended state. The article defines first and second side regions, each side region including one of the first and second side panels and a transverse region of the main portion bordering the respective side panel. An informational image is disposed in at least the first side region, wherein the informational image is legible when the first and second side panels are substantially in the relaxed state.

52 Claims, 15 Drawing Sheets

U.S. PATENT DOCUMENTS

| | | |
|---|---|---|
| 4,078,568 A | 3/1978 | Etes et al. |
| 4,107,364 A | 8/1978 | Sisson |
| 4,140,115 A | 2/1979 | Schonfeld |
| 4,192,311 A | 3/1980 | Felfoldi |
| 4,192,785 A | 3/1980 | Chen et al. |
| 4,209,563 A | 6/1980 | Sisson |
| 4,231,369 A | 11/1980 | Sorensen et al. |
| 4,231,370 A | 11/1980 | Mroz |
| 4,327,731 A | 5/1982 | Powell |
| 4,393,080 A | 7/1983 | Pawelchak et al. |
| 4,463,045 A | 7/1984 | Ahr et al. |
| 4,505,976 A | 3/1985 | Doehnert et al. |
| 4,507,121 A | 3/1985 | Leung |
| 4,515,595 A | 5/1985 | Kievit et al. |
| 4,551,490 A | 11/1985 | Doyle et al. |
| 4,593,053 A | 6/1986 | Jevne et al. |
| 4,610,678 A | 9/1986 | Weisman |
| 4,662,875 A | 5/1987 | Hirotsu et al. |
| 4,663,220 A | 5/1987 | Wisneski et al. |
| 4,673,402 A | 6/1987 | Weisman |
| 4,695,278 A | 9/1987 | Lawson et al. |
| 4,699,146 A | 10/1987 | Sieverding |
| 4,699,622 A | 10/1987 | Toussant et al. |
| 4,705,513 A | 11/1987 | Sheldon |
| 4,710,189 A | 12/1987 | Lash |
| 4,720,415 A | 1/1988 | Vander Wielen et al. |
| 4,738,257 A | 4/1988 | Meyer et al. |
| 4,795,454 A | 1/1989 | Dragoo et al. |
| 4,808,178 A | 2/1989 | Aziz et al. |
| 4,816,025 A | 3/1989 | Foreman |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,963,140 A | 10/1990 | Robertson et al. |
| 4,965,122 A | 10/1990 | Morman |
| 4,981,747 A | 1/1991 | Morman |
| 4,990,147 A | 2/1991 | Freeland |
| 5,026,364 A | 6/1991 | Robertson |
| 5,037,416 A | 8/1991 | Allen et al. |
| 5,064,421 A | 11/1991 | Tracy |
| 5,092,861 A | 3/1992 | Nomura et al. |
| 5,114,781 A | 5/1992 | Morman |
| 5,116,662 A | 5/1992 | Morman |
| 5,133,707 A | 7/1992 | Rogers et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| D331,969 S | 12/1992 | Hunt |
| 5,167,897 A | 12/1992 | Weber et al. |
| D334,426 S | 3/1993 | Meis |
| 5,197,958 A | 3/1993 | Howell et al. |
| 5,221,274 A | 6/1993 | Buell et al. |
| 5,224,405 A | 7/1993 | Pohjola |
| 5,226,992 A | 7/1993 | Morman |
| 5,246,433 A | 9/1993 | Hasse et al. |
| D341,197 S | 11/1993 | Patterson |
| 5,260,345 A | 11/1993 | Desmarais et al. |
| 5,269,775 A | 12/1993 | Freeland et al. |
| 5,330,458 A | 7/1994 | Buell et al. |
| 5,336,545 A | 8/1994 | Morman |
| 5,342,338 A | 8/1994 | Roe |
| 5,358,500 A * | 10/1994 | Lavon et al. ............ 604/385.29 |
| 5,359,525 A | 10/1994 | Weyenberg |
| 5,387,207 A | 2/1995 | Dyer et al. |
| 5,397,316 A | 3/1995 | Lavon et al. |
| 5,468,236 A | 11/1995 | Everhart |
| 5,470,639 A | 11/1995 | Gessner et al. |
| 5,518,801 A | 5/1996 | Chappell et al. |
| 5,540,976 A | 7/1996 | Shawver et al. |
| 5,554,143 A | 9/1996 | Roe et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,634,588 A | 6/1997 | Frode et al. |
| 5,635,191 A | 6/1997 | Roe et al. |
| 5,635,290 A | 6/1997 | Stopper et al. |
| 5,643,588 A | 7/1997 | Roe et al. |
| 5,659,538 A | 8/1997 | Stuebe et al. |
| 5,667,609 A | 9/1997 | Liu |
| 5,681,298 A | 10/1997 | Brunner et al. |
| 5,766,212 A | 6/1998 | Jitoe |
| 5,779,831 A | 7/1998 | Schmitz |
| 5,797,892 A | 8/1998 | Glaug et al. |
| 5,865,823 A | 2/1999 | Curro |
| 5,883,028 A | 3/1999 | Morman et al. |
| 5,897,545 A | 4/1999 | Kline et al. |
| 5,938,648 A | 8/1999 | Lavon et al. |
| 5,957,908 A | 9/1999 | Kline et al. |
| 5,980,087 A | 11/1999 | Brandon et al. |
| 5,997,989 A | 12/1999 | Gessner et al. |
| 6,001,460 A | 12/1999 | Morman et al. |
| 6,004,306 A | 12/1999 | Robles et al. |
| 6,015,764 A | 1/2000 | Mccormack et al. |
| 6,017,537 A | 1/2000 | Alexander et al. |
| 6,075,178 A | 6/2000 | La Wilhelm |
| 6,096,668 A | 8/2000 | Abuto et al. |
| 6,103,647 A | 8/2000 | Shultz et al. |
| 6,107,537 A | 8/2000 | Elder et al. |
| 6,120,487 A | 9/2000 | Ashton |
| 6,120,489 A | 9/2000 | Johnson et al. |
| 6,224,699 B1 | 5/2001 | Bett et al. |
| 6,225,243 B1 | 5/2001 | Austin |
| 6,253,159 B1 | 6/2001 | Bett et al. |
| 6,264,641 B1 | 7/2001 | Van Gompel et al. |
| 6,266,436 B1 | 7/2001 | Bett et al. |
| 6,297,424 B1 | 10/2001 | Olson |
| 6,307,119 B1 | 10/2001 | Cammarota |
| 6,313,372 B1 | 11/2001 | Suzuki |
| 6,428,526 B1 | 8/2002 | Heindel et al. |
| 6,432,098 B1 | 8/2002 | Kline et al. |
| 6,443,940 B1 | 9/2002 | Ashton et al. |
| 6,444,064 B1 | 9/2002 | Henry et al. |
| 6,448,467 B1 | 9/2002 | Herrlein et al. |
| 6,465,073 B1 | 10/2002 | Morman et al. |
| 6,479,154 B1 | 11/2002 | Walton et al. |
| 6,503,236 B1 | 1/2003 | Uitenbroek et al. |
| 6,579,274 B1 | 6/2003 | Morman et al. |
| 6,596,918 B1 | 7/2003 | Wehrle |
| 6,617,016 B2 | 9/2003 | Zhang et al. |
| 6,623,837 B2 | 9/2003 | Morman et al. |
| 6,627,564 B1 | 9/2003 | Morman et al. |
| 6,642,427 B2 | 11/2003 | Roe et al. |
| 6,680,265 B1 | 1/2004 | Smith et al. |
| 6,702,795 B2 | 3/2004 | Klemp |
| 6,710,221 B1 | 3/2004 | Pierce |
| 6,743,314 B2 | 6/2004 | Henry et al. |
| 6,766,817 B2 | 7/2004 | Da Silva |
| 6,772,708 B2 | 8/2004 | Klofta |
| 6,811,865 B2 | 11/2004 | Morman et al. |
| 6,849,324 B2 | 2/2005 | Meece et al. |
| 6,875,710 B2 | 4/2005 | Eaton et al. |
| 6,904,865 B2 | 6/2005 | Klofta et al. |

| | | |
|---|---|---|
| 6,905,488 B2 | 6/2005 | Olson |
| 6,909,028 B1 | 6/2005 | Shawver et al. |
| 6,918,404 B2 | 7/2005 | Dias Da Silva |
| 6,942,894 B2 | 9/2005 | Alberg et al. |
| 6,955,733 B2 | 10/2005 | Miller et al. |
| 6,957,160 B2 | 10/2005 | Miller et al. |
| 6,960,834 B2 | 11/2005 | Nakamura et al. |
| 7,056,411 B2 | 6/2006 | Desai et al. |
| 7,066,586 B2 | 6/2006 | Da Silva |
| 7,123,981 B2 | 10/2006 | Dollevoet et al. |
| 7,169,137 B2 | 1/2007 | Shimada |
| 7,223,818 B2 | 5/2007 | Autran et al. |
| 7,285,255 B2 | 10/2007 | Kadlec et al. |
| 7,301,036 B2 | 11/2007 | Parmee et al. |
| 2002/0062117 A1 | 5/2002 | Raufman et al. |
| 2002/0111596 A1 | 8/2002 | Fletcher et al. |
| 2002/0138062 A1 | 9/2002 | Kuen et al. |
| 2003/0065298 A1 | 4/2003 | Krishnaswamy-Mirle et al. |
| 2003/0073966 A1 | 4/2003 | Sosalla et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0120240 A1 | 6/2003 | Buell et al. |
| 2003/0158532 A1 | 8/2003 | Magee et al. |
| 2003/0162458 A1 | 8/2003 | Tsujiyama et al. |
| 2003/0167049 A1 | 9/2003 | Gibbs |
| 2004/0064113 A1 | 4/2004 | Erdman |
| 2004/0092902 A1 | 5/2004 | Hoffman et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0191118 A1 | 9/2004 | Mody |
| 2004/0193113 A1 | 9/2004 | Gillis et al. |
| 2005/0027274 A1 | 2/2005 | Suzuki et al. |
| 2005/0065489 A1 | 3/2005 | Driskell et al. |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0214461 A1 | 9/2005 | Desai et al. |
| 2005/0222546 A1 | 10/2005 | Vargo et al. |
| 2006/0004333 A1 | 1/2006 | Olson |
| 2006/0025737 A1 | 2/2006 | Song et al. |
| 2006/0068168 A1 | 3/2006 | Olson et al. |
| 2006/0069361 A1 | 3/2006 | Olson et al. |
| 2006/0069362 A1 | 3/2006 | Odorzynski et al. |
| 2006/0212010 A1 | 9/2006 | Roe et al. |
| 2006/0212018 A1 | 9/2006 | Roe et al. |
| 2006/0247594 A1 | 11/2006 | Nickel et al. |
| 2006/0264858 A1 | 11/2006 | Roe et al. |
| 2007/0032766 A1 | 2/2007 | Liu et al. |
| 2007/0073261 A1 | 3/2007 | Ashton et al. |
| 2007/0287982 A1 | 12/2007 | Lodge et al. |
| 2007/0287983 A1 | 12/2007 | Lodge et al. |

FOREIGN PATENT DOCUMENTS

| | | |
|---|---|---|
| EP | 0 547 497 A | 6/1993 |
| EP | 0 937 446 A2 | 8/1999 |
| EP | 1023024 A1 | 8/2000 |
| EP | 0 776 645 B1 | 3/2002 |
| EP | 1216673 A1 | 6/2002 |
| EP | 1222907 A2 | 7/2002 |
| EP | 1 287 799 A2 | 3/2003 |
| EP | 1356798 A1 | 10/2003 |
| EP | 1279357 B1 | 9/2005 |
| JP | 2004 141640 A | 5/2004 |
| WO | WO 94/13235 A1 | 6/1994 |
| WO | WO-95/16746 A1 | 6/1995 |
| WO | WO9516746 A1 | 6/1995 |
| WO | WO 99/22688 | 5/1999 |
| WO | WO 00/00233 A1 | 1/2000 |
| WO | WO 00/15169 A1 | 3/2000 |
| WO | WO 00/35401 | 6/2000 |
| WO | WO-00/37006 A1 | 6/2000 |
| WO | WO-01/21126 A1 | 3/2001 |
| WO | WO 01/41691 A1 | 6/2001 |
| WO | WO 01/95845 A1 | 12/2001 |
| WO | WO 02/49564 A1 | 6/2002 |
| WO | WO-02/91968 A2 | 11/2002 |
| WO | WO 2004/028403 A2 | 4/2004 |
| WO | WO 2005/037159 A | 4/2005 |
| WO | WO-2005/041834 A1 | 5/2005 |
| WO | WO-2005/102239 A1 | 11/2005 |
| WO | WO-2006/017518 A2 | 2/2006 |
| WO | WO-2006/017674 A1 | 2/2006 |
| WO | WO-2006/028911 A1 | 3/2006 |
| WO | WO-2006/127519 A2 | 11/2006 |

OTHER PUBLICATIONS

U.S. Appl. No. 11/083,606, filed Mar. 18, 2005, Donald Carroll Roe et al.

PCT Search Report and Written Opinion, PCT/US2006/019580, mailed Jun. 11, 2006, 17 pages.

PCT Search Report, PCT/US2006/009303, mailed Oct. 7, 2007, 6 pages.

* cited by examiner

PULL-ON WEARABLE ARTICLE WITH INFORMATIONAL IMAGE

FIELD OF THE DISCLOSURE

The present disclosure relates to pull-on wearable articles, such as disposable, absorbent pull-on diapers and the like. More particularly, the present disclosure relates to visual features for initiating a cognitive response by a user of such articles.

BACKGROUND OF THE DISCLOSURE

Wearable articles, such as absorbent, disposable diapers for infants and small children and adult incontinence products, have long been known in the art. These articles are designed to absorb and contain body exudates such as urine and fecal matter. Ideally these products fit snugly and prevent leakage of exudates.

Typically, conventional diaper products for infants and small children have included a front waist portion, and a rear waist portion which are releasably connected about the hips of the user during use by fasteners such as adhesive tape fasteners or hook and loop type fasteners. Commonly such diapers are applied by laying the baby on its back, positioning the diaper between the baby's legs and fastening the fasteners about the waist.

More recently, there have been several prior art disposable absorbent articles of the "pull-on" or "pants" type. These articles are typically placed on a user in a closed waist configuration, and therefore are designed to be pulled up over the hips and buttocks of the user into position around the waist and between the legs. Ideally, application would be substantially accomplished by the child, however these articles are typically applied at least partially by the caregiver due to the difficulty involved. A caregiver will often perform or assist in one or more of the following actions: (1) threading the user's legs through leg holes in the article; (2) pulling the article over the user's hips and buttocks; and (3) correcting or adjusting the fit of the article once it is in position. Typically, such pull-on articles have a stretchable portion, such as a stretchable side panel which expands to allow the article to be pulled over the hips and then elastically retracts to provide a conforming fit of the article. A variation of the pull-on articles includes refastenable seamed areas, such as refastenable side seams. While these alternative articles may be opened by unfastening the seams, they are typically intended to be applied to a user while in the closed configuration, and therefore include a stretchable portion as noted above.

Pull-on absorbent articles are often intended for use by children as they transition from wearing conventional diapers to underwear. As children grow and develop, they achieve the capability to dress themselves. Young children and babies, especially once they begin walking, commonly wear pull-on diapers and/or training pants, which are typically easier for a user to apply and remove in a standing position, and therefore emulate underwear.

It is desirable for pull-on diapers and training pants to facilitate the overall dressing learning process by making it easier for the child to successfully apply a pull-on product. Due to physiological, psychological, or other factors, most children, particularly in the 12-30 month age range, are naturally inclined to grab the most easily visible and accessible portion of the pull-on product, which is the front waist region. Because the pull-on article must be pulled over the buttocks and hips, the tendency to pull at the front of the product often leads to failure and frustration because this action increases the circumferential tension in the back of the diaper, causing it to lodge tightly at the bottom of the buttocks. Further, no vertical tension is applied to the area that could dislodge the article, which is the back waist region of the article. Accordingly, it is more advantageous for the child to grasp and pull the product from the sides, thereby distributing vertical pulling force to both the front and back regions.

It is advantageous, therefore, to provide a pull-on article that encourages grasping at the sides during use. U.S. Pat. No. 6,702,795 to Klemp proposes a disposable absorbent article with stretchable side waist regions marked with decorative or instructional printing. The side waist regions have a contracted configuration but are stretchable to an extended configuration. Klemp discloses that decorative or instructional printing is applied to the side waist regions such that the printing is most observable in the extended configuration (i.e., when worn on the waist) but is less observable and unobscured in the contracted configuration (i.e., when not worn on the waist). Prior to placement on the waist, however, a pull-on article is typically placed around the ankles or knees of the child, and therefore is typically in the substantially contracted or relaxed state. It is at this point in the application process that the child needs to quickly and correctly identify the location at which to grasp the product to enable the pulling-up motion. Thus, the printing disclosed in Klemp provides limited, if any, instructional assistance to a user prior to pulling into place around the waist, since the printing will be less observable or obscured when the Klemp article is contracted. Consequently, a need exists for a pull-on wearable article that conveys instructional or other information to a user when the article is in a configuration observable at the point in the application process when the child is deciding where to grasp the article in preparation to pull it up.

DETAILED DESCRIPTION

Figure 1:
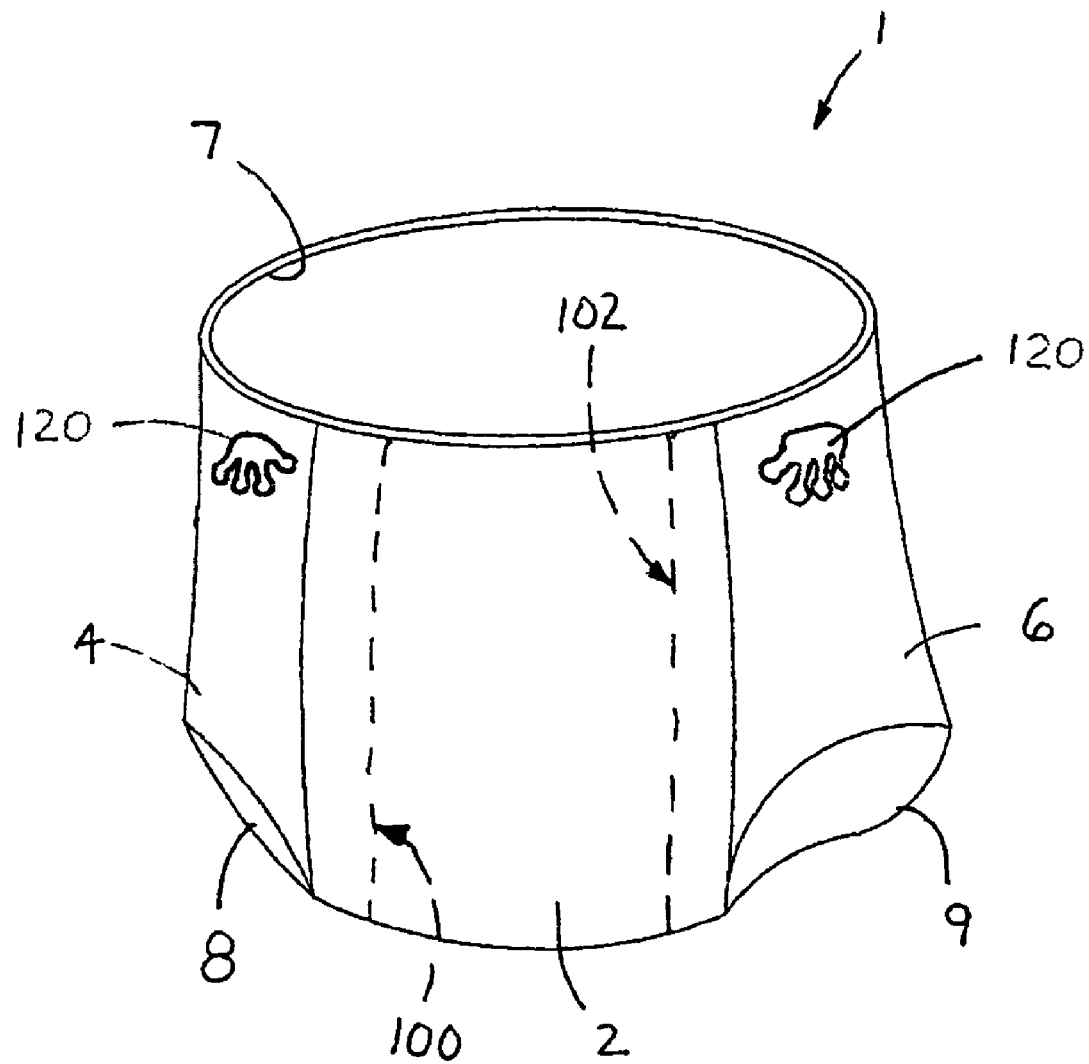
FIG. 1 is a perspective view of a pull-on wearable article according to the present disclosure.

As used herein, the phrase "wearable article" refers to an article configured such that it has a waist opening and a pair of leg openings. This configuration may be permanent as in the case of conventional underwear, or may be temporary as in the case of a training pant with openable seams for removal. Additionally, pull-on articles can be constructed with refastenable features allowing the article to have both a closed pant-like configuration and one or more configurations which are open or not pant like. Wearable articles include durable and disposable absorbent articles, such as disposable diapers, as well as partially or non-absorbent articles such as training pants or disposable pull-on diapers.

As used herein, the phrase "pull-on application" refers to the method of placing an article with a closed configuration on a user's waist region by threading the user's legs through the waist opening and pulling the article along the legs and over the hips and buttocks. The article may be permanently in the closed configuration or may be capable of being placed in an open configuration but intended to be applied while in a closed configuration.

As used herein, the phrase "absorbent article" refers to devices that absorb and contain liquid, and more specifically, refers to devices that are placed against or in proximity to the body of the user to absorb and contain the various exudates discharged from the body.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "disposable" describes absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "longitudinal" is a direction running parallel to the maximum linear dimension of the article and includes directions within ±45° of the longitudinal direction. The terms "lateral" or "transverse" indicate a direction that is orthogonal to the longitudinal direction. The "Z-direction" is orthogonal to both the longitudinal and lateral directions. The "x-y plane" refers to the plane congruent with the longitudinal and transverse directions.

The term "disposed" is used herein to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein the term "refastenable" refers to the attachment of two or more elements or portions of elements together in a manner in which they can be separated and re-attached successively without substantial degradation of fastener performance or damage to surrounding components of the article which would impair its continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening or tack may be reduced significantly from fastening to refastening in absolute terms, but that such reduction is not "substantial degradation" of fastener performance if the resulting refastened strength is sufficient for its purpose of use in a disposable absorbent article.

As used herein, the term "impermeable" generally refers to articles and/or elements that are not penetrative by fluid through the entire Z-directional thickness of the article under pressure of 0.14 lb/in$^2$ or less. The impermeable article or element also may not be penetrative by fluid under pressures of 0.5 lb/in$^2$ or less. The impermeable article or element may also not be penetrative by fluid under pressures of 1.0 lb/in$^2$ or less.

As used herein, the term "adhesive" or "typical adhesive" are interchangeable and refer to a material which demonstrates connection when applied to another material generally (e.g. material is not specially selected). Adhesive materials connect to other materials generally and no particularly selected properties of the other material are necessary for such tack to be demonstrated. Generally, typical adhesive materials used in disposable absorbent articles demonstrate such tack either at certain temperatures (such as a hot melt adhesive) or under pressure (a pressure sensitive adhesive).

As used herein the term "extensible" refers to materials which elongate or increase in at least one dimension when subject to an external pulling force.

As used herein the terms "elastic" or "stretchable" are intended to be interchangeable and refer to materials which are extensible and which also return to substantially their original dimensions when the external pulling force is removed.

As used herein the term "extendable" refers to materials which are extensible and which are preferably at least partially elastic.

As used herein, the term "legible" refers to an image, or an image in a particular state, that is sufficiently clear, distinct, and unambiguous so that it is capable of being rapidly and/or easily read or deciphered.

Pull-on wearable articles are disclosed herein having extendable side panels and an informational image. The informational image is legible with the extendable side panels in a substantially relaxed state. Prior to placement on a user, and prior to pulling the product over the hips and buttocks (i.e., when in a "threaded" state), the article will be in or substantially in the relaxed state, and therefore the informational image will be legible to the user at the appropriate point in the application process. In one embodiment, the informational image includes an attention attracting graphic that triggers a cognitive response in a pre-literate child or other user to grasp the article in the vicinity of the image. The article may further include a texture feature which, together with the informational image, forms a composite image. The texture feature may form a part of the composite image that is separate from the informational image or may be coincident with the informational image to enhance its appearance, such as by imparting a layered, three-dimensional, or other visual effect to enhance the image. Furthermore, the image may include a cognitively functional graphic that communicates to the user instructions or other information regarding the article.

While the embodiments presented in this application are described and illustrated as absorbent articles such as disposable pull-on diapers or training pants, it will be appreciated that this disclosure is not so limited but instead includes any pull-on wearable article, as defined herein.

Referring to FIG. 1, an exemplary pull-on wearable article 1 is illustrated having a closed construction. The article 1 includes a main portion 2 and first and second side panels 4 and 6. The main portion 2 and side panels 4, 6 generally define a waist opening 7 and a pair of leg openings 8 and 9, to form a pull-on or pant-like article. As discussed in greater detail below, each of the side panels 4 and 6 may be extendable (i.e., extensible and preferably at least partially elastic, as defined above), to facilitate placement and removal. The article 1 has a closed construction. The closed construction is permanent in the sense that the side panels 4, 6 are intended to maintain the closed configuration prior to and during use. As such, the article 1 is supplied, placed, and worn in a closed configuration. The side panels 4, 6 may be frangible or frangibly connected to the main portion so that the article 1 may be opened during removal and/or preparation for disposal.

Figure 2:
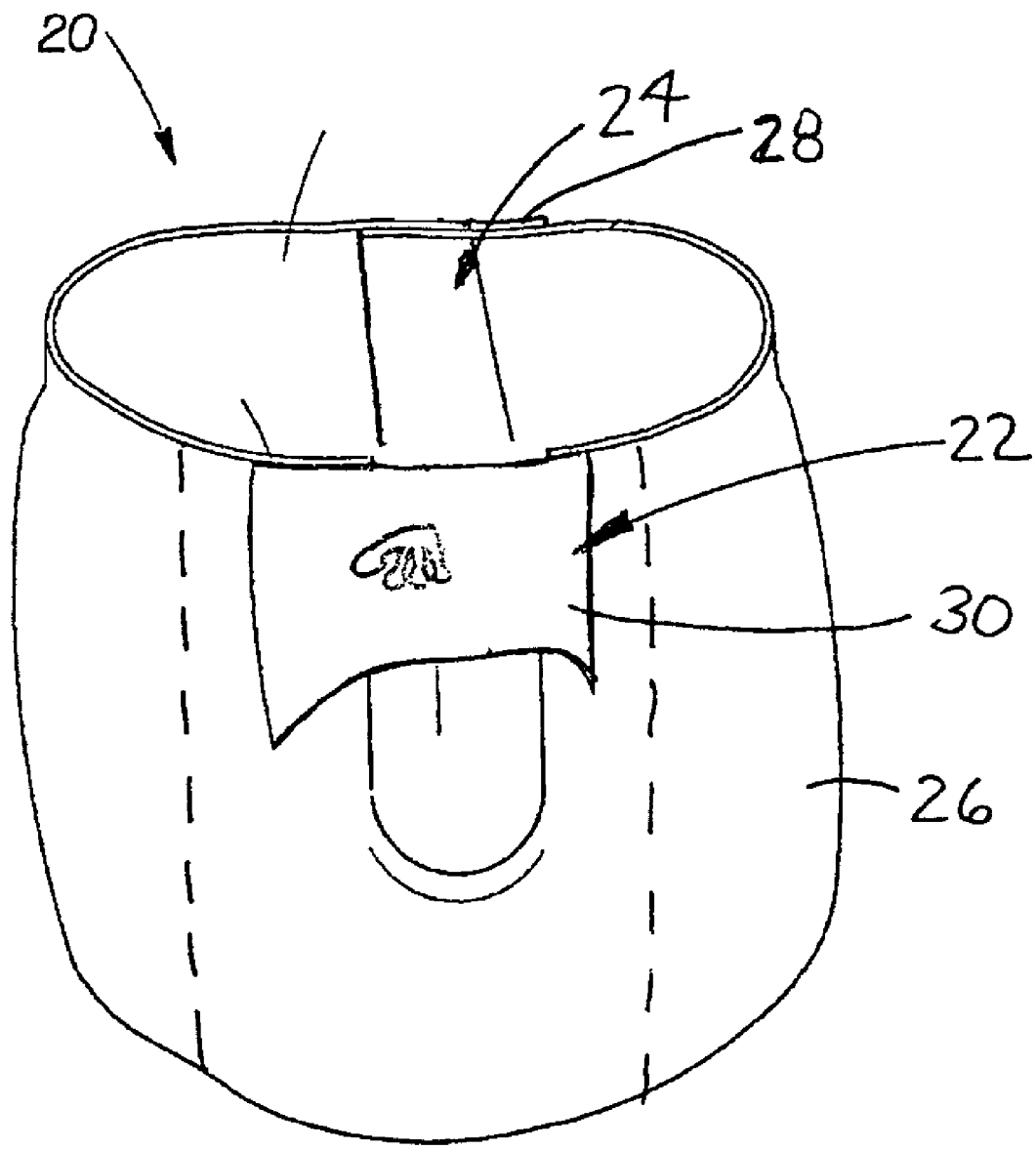
FIG. 2 is a perspective view of an alternative embodiment of a pull-on wearable article having a releasable fastener.
Figure 3:
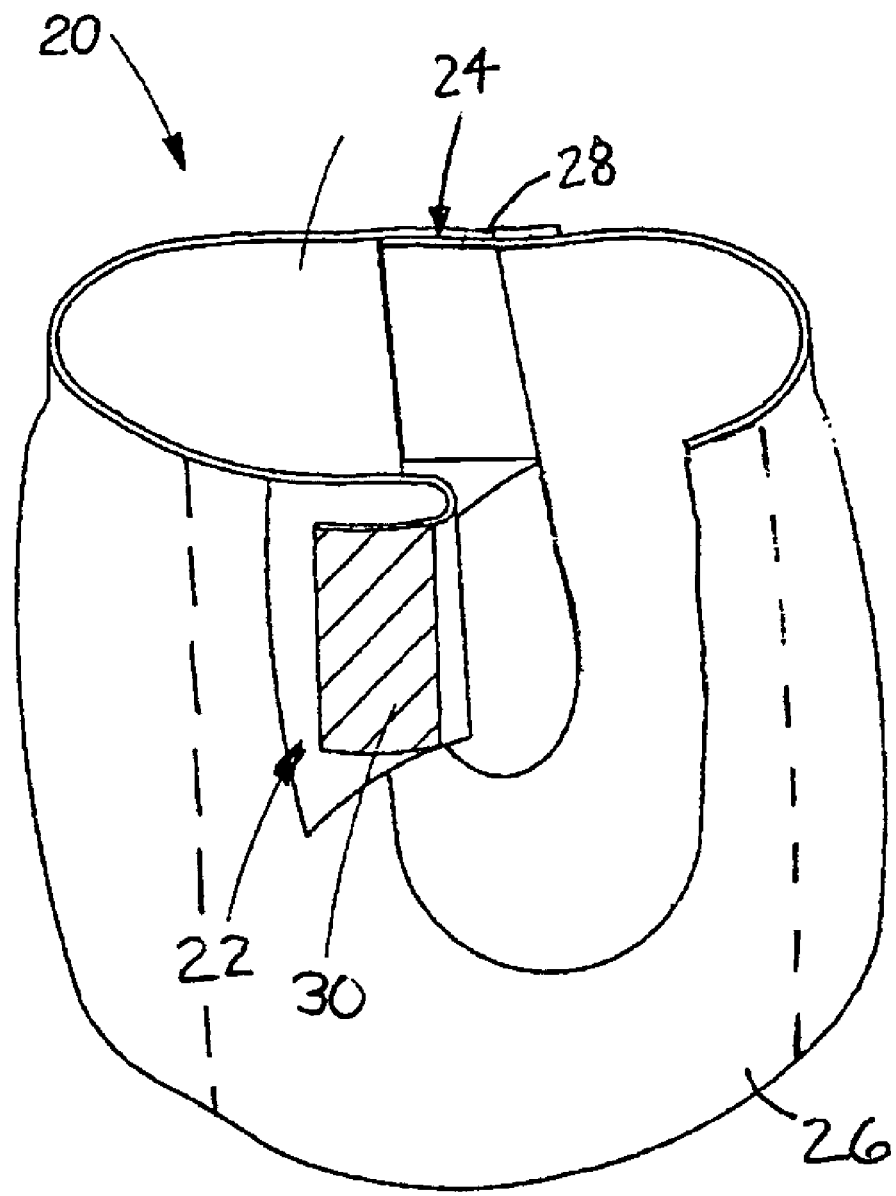
FIG. 3 is a perspective view of the article of FIG. 2 with a fastener released.

In an alternative embodiment illustrated in FIGS. 2 and 3, a pull-on wearable article 20 may be selectively placed in both open and closed configurations. The article 20 includes side panels 22, 24 that are releasably fastenable to a main portion 26, allowing the side panels 22 and 24 to be opened and re-closed along either or both of side attachment areas 28 and 30. While the embodiment of FIGS. 2 and 3 show side panels 22, 24 releasably attachable to a front of the main portion, they may alternatively or additionally be releasably attachable to a rear of the main portion. The side panels 22 and 24 may be extendable to facilitate pull-on application and removal.

In this embodiment, the side attachment areas 28, 30 may be fastened to the main portion 26 to create a closed configuration defining waist and leg openings similar to the closed article 1 illustrated in FIG. 1. Additionally, the side attachment areas 28, 30 may be unfastened, such as the right side attachment area 30 as illustrated in FIG. 3. When one or both of the side attachment areas 28, 30 is unfastened so that the respective side panel 22, 24 is opened, the article 20 is said to be an open configuration. The respective side panels 22, 24 of the article 20 may be either separately attached to the main portion 26 or may be made integrally with the main portion 26. The article 20 may be provided to the user in either of the open or closed configurations. If provided in the open configuration, the user or a caregiver may place the article 20 in the closed configuration prior to placement on the user. If provided in the closed configuration, the user or caregiver may adjust the waist opening size by opening one or both attachment areas 28, 30 and reattaching in a different position. Even with such adjustment, the article 20 is preferably returned to the closed configuration prior to placement on a user.

Figure 4:
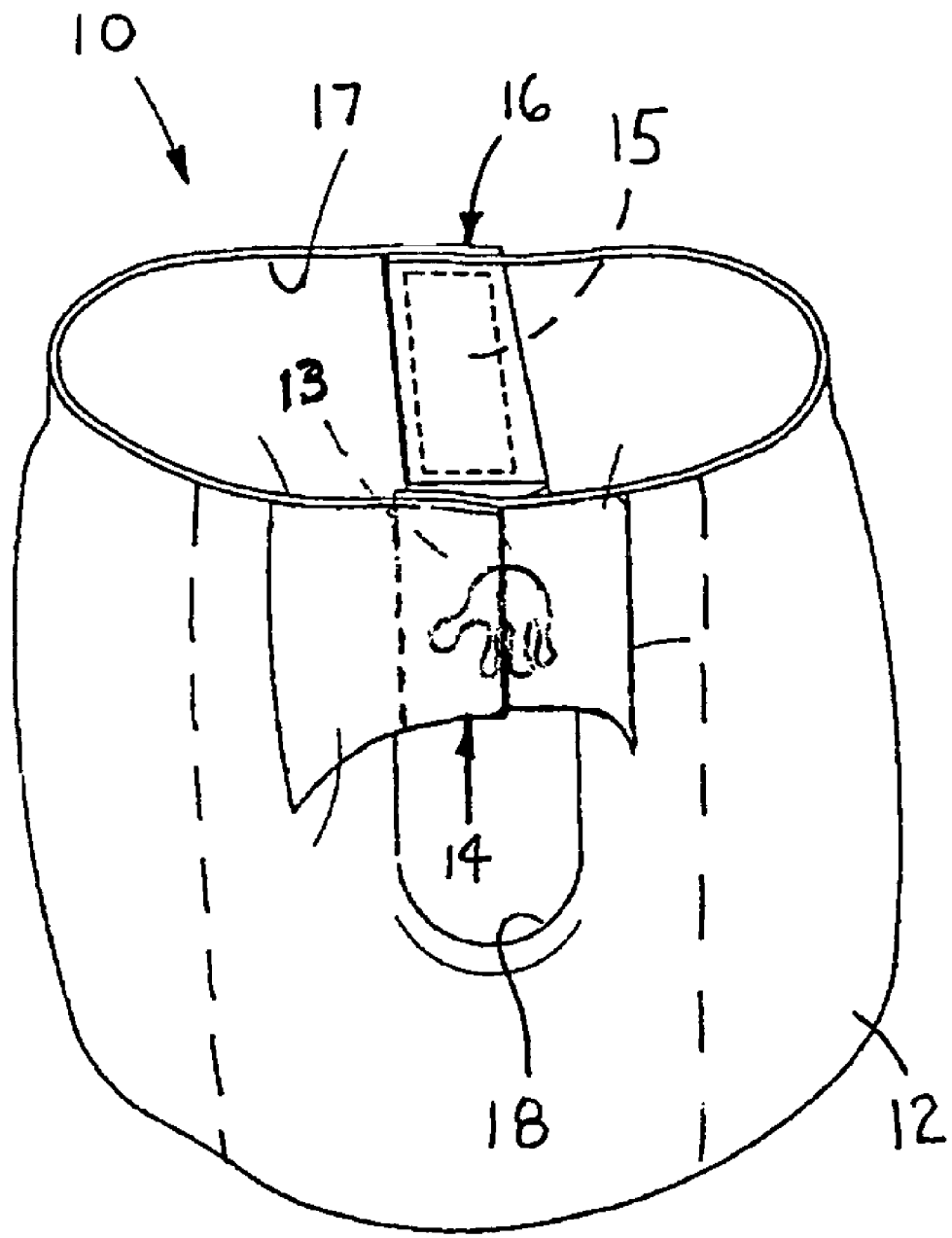
FIG. 4 is a perspective view of an alternative embodiment of a pull-on wearable article having a releasable fastener.
Figure 5:
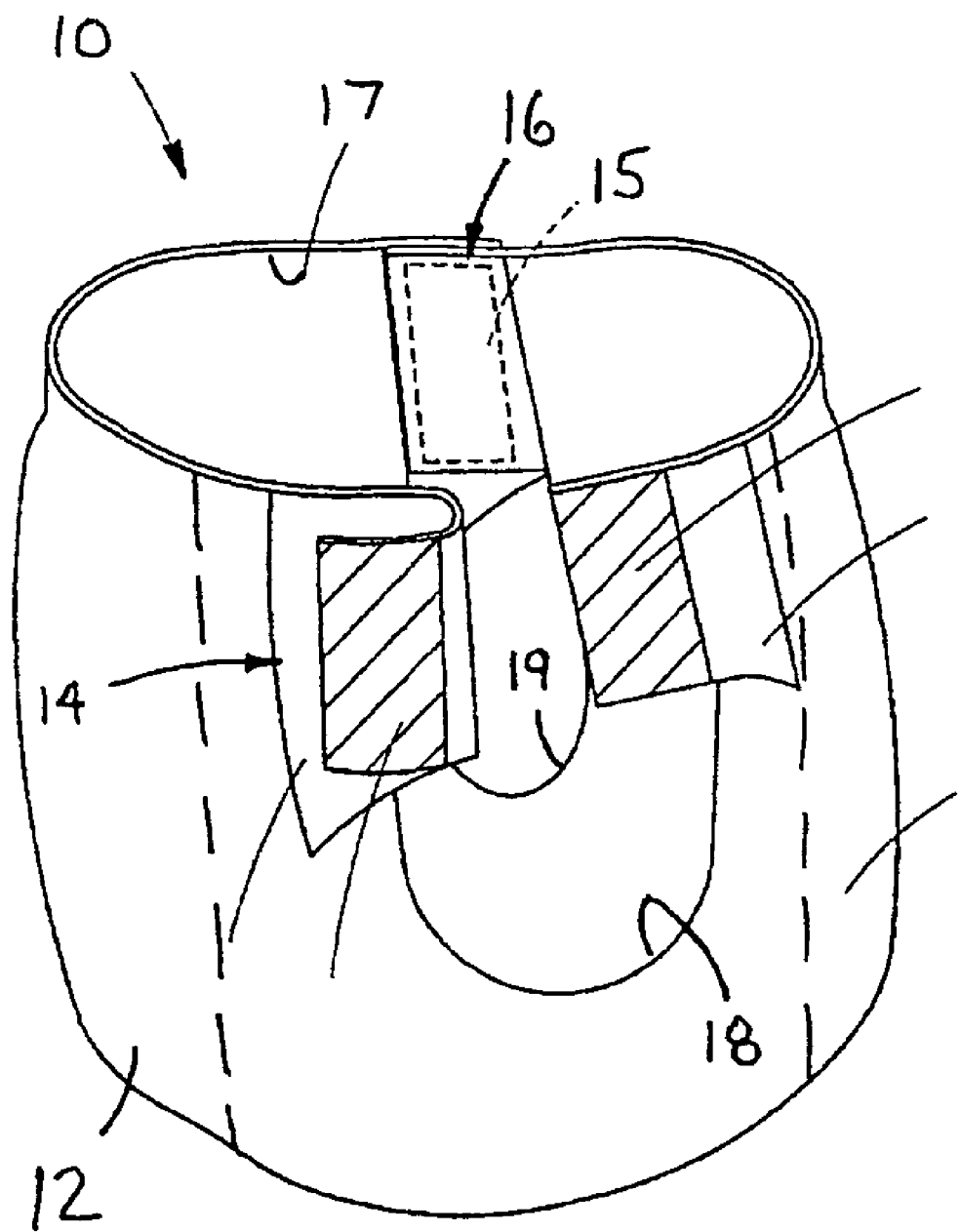
FIG. 5 is a perspective view of the article of FIG. 4 with a fastener released.
Figure 6:
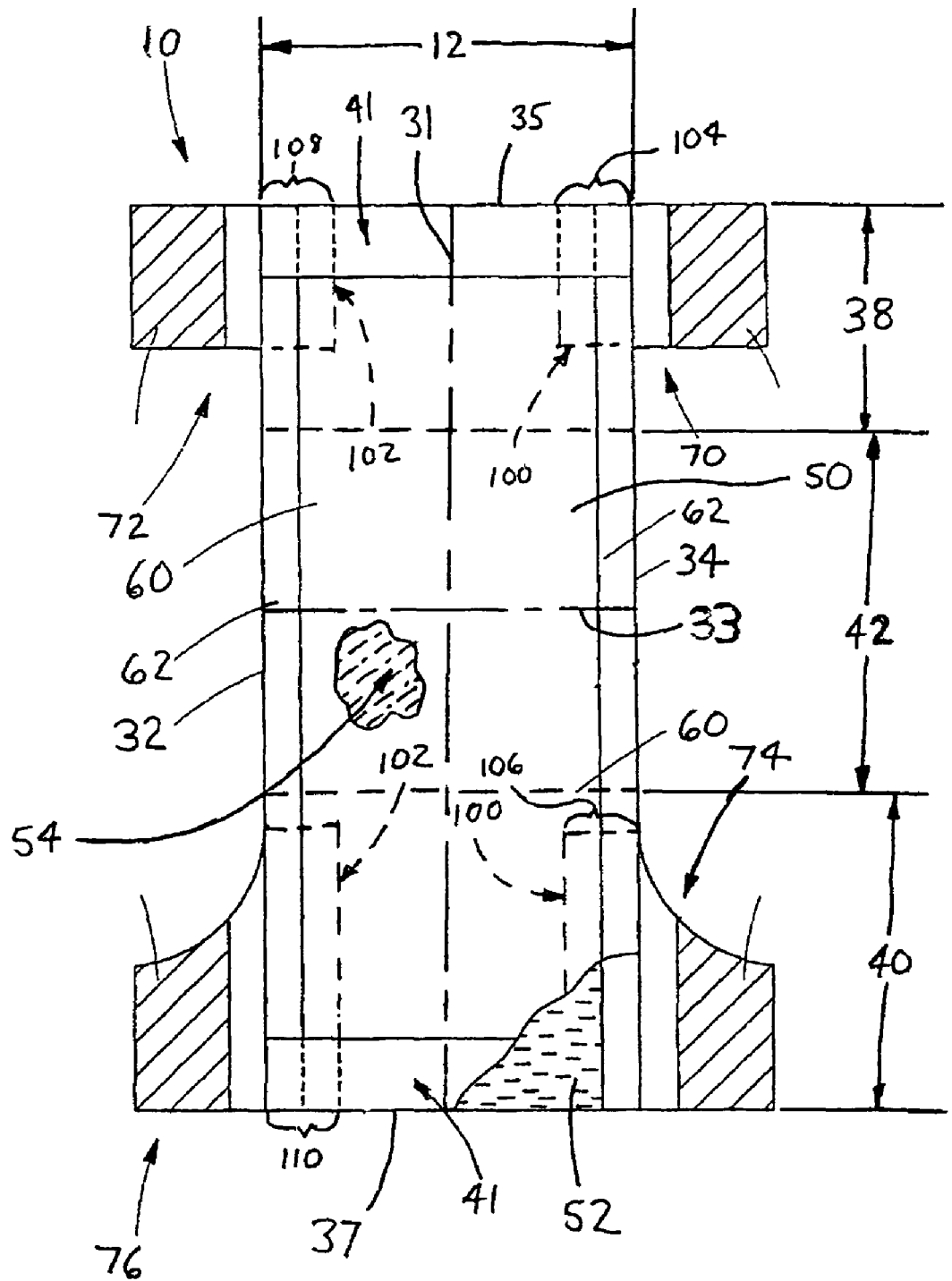
FIG. 6 is a plan view of the pull-on wearable article of FIG. 1 laid flat in an open configuration.

In a further alternative embodiment illustrated in FIGS. 4-6, an article 10 has side panels 14, 16 that may be opened or closed, similar to the embodiment illustrated in FIGS. 2 and 3. In this embodiment, the side panels 14, 16 include front panel portions 70, 72 and rear panel portions 74, 76. The front and rear panel portions 70, 72, 74, 76 may be coupled to or extend continuously from respective front and rear parts of the main portion 12. Each side panel 14, 16 may be extendable to facilitate placement and removal, and may be provided with a refastenability feature allowing the side panels 14, 16 to be opened and re-closed along either or both of side attachment areas 13, 15. One side panel 14, 16 may be less extendable or non-extendable. Furthermore, a portion of one or both side panels 14, 16 may be more or less extendable than a remainder of that side panel. The relative extendibility of the side panels or portions of a side panel are not limited to this embodiment, but may be provided in other types of articles having extendable side panels, including those described in connection with the embodiments of FIGS. 1-3.

When the side attachment areas 28, 30 are fastened to close the side panels 14, 16 (as shown in FIG. 4), the article 10 has a closed configuration defining a waist opening 17 and a pair of leg openings 18, 19, to form a pull-on or pant-like article. Either or both of the side panels 14, 16 may be opened (such as side panel 14 of FIG. 5) to place the article 20 in an open configuration. Additional details of refastenable side panels, such as the side panels described with respect to FIGS. 2-6, can be found in co-pending U.S. Pat. No. 6,432,098 issued to Kline et al. on Aug. 13, 2002 entitled "Absorbent Article Fastening Device," the disclosure of which is incorporated by reference herein.

Referring to FIG. 6, the article 10 is shown laid flat in the open configuration. In this configuration, the article 10 may be described with reference to a longitudinally extending axis 31 and a laterally (or transversely) extending axis 33. Along the longitudinal axis 31, the article 10 includes a front waist region 38 having a front edge 35, a rear waist region 40 having a rear edge 37, and a crotch region 42 extending between the front and rear waist regions 38, 40. The crotch region 42 is that portion of the article 10 which, when the article 10 is worn, is generally positioned between the legs of the user. While the regions 38, 40, 42 are illustrated as each comprising roughly one-third of the overall longitudinal length of the article 10, the present disclosure is not limited to this exemplary embodiment, as each region may have any suitable length in relation to the overall longitudinal length. Along the lateral direction, the main portion 12 of article 10 is bounded by a pair of longitudinal edges, left edge 32 and right edge 34.

The waist regions 38, 40 may be provided with elastic gathering features, padding features, containment features, or any other features (including stretchable waistbands) typically provided in the waist regions of disposable absorbent articles of this type, a wide variety of which are known in the art. An example of such a feature is shown in FIG. 6 as waist feature 41 (including front and rear sections). As with the waist regions, the crotch region 42 may be provided with any of the features typically provided on disposable absorbent articles of this type. Examples of such features typically employed in the art are leg elastics, barrier containment structures (such as standing leg cuffs or barrier leg cuffs), graphics, notches for fit or appearance, etc.

The main portion 12 of the article 10 typically comprises at least a liquid pervious topsheet 50, a liquid impervious backsheet 52, and at least a portion of an absorbent core 54 encased between the topsheet 50 and the backsheet 52. For unitary absorbent articles, this basic assembly comprises the main structure of the diaper with other features added to form the main portion 26 and ultimately the article 10 as a whole. While the topsheet 50, the backsheet 52, and the absorbent core 54 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999.

The topsheet 50 is compliant, soft feeling, and non-irritating to the user's skin. Further, the topsheet 50 is liquid pervious permitting liquids (e.g., urine) to readily penetrate through its thickness. A suitable topsheet may be manufactured from a wide range of materials, such as porous foams; reticulated foams; apertured plastic films; apertured non-woven webs; or woven or non-woven webs of natural fibers (e.g., wood or cotton fibers), synthetic fibers (e.g., polyester or polypropylene fibers), or a combination of natural and synthetic fibers. Preferably, the topsheet 50 is made of a hydrophobic material to isolate the user's skin from liquids contained in the absorbent core 54 (i.e., prevent "rewet"), unless the article is intended to provide at least a partial wetness sensation to the user, as is desirable in certain training pant articles.

The topsheet 50 may be fully or partially elasticized or may be foreshortened so as to provide a void space between the topsheet 50 and the core 54. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets".

The absorbent core 54 may comprise any absorbent material that is generally compressible, conformable, non-irritating to the user's skin, and capable of absorbing and retaining liquids such as urine and other certain body exudates. The absorbent core 54 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; superabsorbent fibers; or any other known absorbent material or combinations of materials.

Exemplary absorbent structures for use as the absorbent cores (either single layer, or multi layer composite structures) are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997.

The backsheet 52 is generally that portion of the article 10 positioned adjacent the outer facing surface of the absorbent core 54. Backsheet 52 prevents the exudates absorbed and contained therein from soiling items that may contact the article 10, such as bed sheets and undergarments. In preferred embodiments, the backsheet 52 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the article 10 while still preventing exudates from passing through the backsheet 54. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by Tredegar Industries under the designation EXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996.

Backsheet 52 may also consist of more than one layer. For example, a backsheet outer layer (often referred to simply as the backsheet) may be made of a soft, non-woven material and a backsheet inner layer may be made of a substantially impermeable film. Alternatively, the backsheet may simply comprise one or more liquid permeable layers, in which case it may be preferable to include an additional, substantially impermeable layer between the absorbent core 54 and the backsheet 52 to provide containment. Examples of such a layer include substantially impermeable films, a wax layer (i.e., a wax coating applied to the absorbent core 54 or an element thereof), or other suitable material, further examples of which are described in U.S. Published Application No. US2003/0065298 entitled "Absorbent Barrier Structures Having a High Convective Air Flow Rate and Articles Made Therefrom" to Krishnaswamy-Mirle et al., published on Apr. 3, 2003.

Even if not referred to as the backsheet, pant like articles desirably have an outer cover layer of soft material. This layer may extend beyond the edges of the main portion 12 (e.g. it may also extend into and cover the side panels) or it may be coterminous with other layers of the main portion 12. If the backsheet 52 consists of multiple layers, the layers may be coterminous with each other or may have different dimensions. Adhesive, or any other suitable material or method, may be used to join backsheet layers together. While a variety of backsheet configurations are contemplated herein, it would be obvious to those skilled in the art that various other changes and modifications can be made without departing from the spirit and scope of the invention.

The article 10 may also include such other features as are known in the art including cuffs, waist cap features, elastics and the like to provide better fit, containment and aesthetic characteristics. Such additional features are well known in the art and are described in U.S. Pat. No. 3,860,003; and U.S. Pat. No. 5,151,092.

For example, article 10 may include barrier cuffs 60 which provide improved containment of liquids and other body exudates. Barrier cuffs 60 may also be referred to as barrier leg cuffs, inner leg cuffs, containment flaps, or "stand-up" elasticized flaps. U.S. Pat. Nos. 4,808,178 and 4,909,803 issued to Aziz et al. on Feb. 28, 1989 and Mar. 20, 1990, respectively, describe disposable diapers having "stand-up" elasticized flaps that improve the containment of the leg regions.

Additionally, article 10 may include gasketing cuffs 62 which also provide improved containment of liquids and other body exudates. Gasketing cuffs 62 may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Barrier cuff 60 and gasketing cuff 62 may both be provided by way of a dual cuff, as exampled in U.S. Pat. Nos. 4,695,278 and 4,795,454 issued to Lawson on Sep. 22, 1987 and to Dragoo on Jan. 3, 1989, respectively. Any of the elastic materials known in the art typically employed in such cuff structures are suitable for use in articles of the present invention is cuff structures are employed. Cuffs may be joined to the main portion 26 using any suitable means known in the art.

As previously noted, the side panels may be integral with the main portion 12 (that is they may be continuous extensions of one or more of the layers of the main portion 12) or they may be separately attached to the main portion 12 (such as a completely separate elastic laminate attached to a peripheral part of the main portion). Alternatively, the side panels may be made of multiple components or layers, some of which are discrete (either attached separately to the main portion or separated therefrom by a gap) and some of which are continuous. An example of this type of construction is an article provided with an outer non-woven cover which completely covers all areas of the article 10 including the side panels 14 and 16 and the main portion 12, such as the article disclosed in U.S. Published Application No. US2003/0065298.

The side panels 14 and 16 together with the main portion 12 form the pull-on article 10 having a waist opening 17 and a pair of leg openings 18 and 19, when said pull-on article is in a closed configuration. In the embodiment illustrated in FIG. 6, the side panels 14, 16 have separate front panel portions 70, 72, and rear panel portions 74, 76. The front and rear panel portions 70, 72, 74, 76 may comprise extensions of the front and rear waist regions, respectively, of the main portion 12, or may comprise separate components that are coupled to the front and rear waist regions. Adjacent edge regions of a respective pair of front and rear panel portions may be releasably fastenable as illustrated in FIGS. 4 and 5, or may be permanently joined to form a seam, as discussed in greater detail below with reference to FIG. 10. Consistent with its use above, the term "permanent" indicates that the edge regions are sufficiently joined to maintain connection prior to and during use, however at least one edge region may be frangible or the edge regions may be frangibly connected to facilitate removal and/or disposal. Alternatively, the front and rear panel portions may simply be different parts of a unitary side panel, as illustrated in FIG. 1 that is provided as a separate component or as an extension of either the front or rear waist region of the main portion 12.

Returning to FIG. 6, the front panel portions 70, 72 are disposed generally transversely outward from said longitudinal edges 32 and 34 of said main portion 12 at or near the front waist region 38. Similarly the rear panel portions 74 and 76 are disposed generally transversely outward from said longitudinal edges 32 and 34 of said main portion 12 at or near the rear waist region 40. In this manner the respective waist regions together with the panel portions (both front and rear) form a complete waist opening when the front and rear waist portions are joined. Similarly, the main portion 12 and the side panels in combination also form leg openings 18 and 19 in a similar manner.

Preferably, the side panels 14 and 16 may be extensible or more preferably elastic. The side panels 14, 16 may be provided in a variety of forms. For example, each side panel may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the non-woven layer permanently, but the elastomeric element temporarily. Alternatively or additionally, the activation process may disrupt or otherwise break bonds within the non-woven layer such that the disrupted non-woven layer does not substantially impede elongation of the elastomeric element. The non-woven layer may be integral with at least a portion of the backsheet of the main portion, in which case the elastomeric element may be attached to the non-woven layer and the non-woven/elastomeric element laminate is subsequently activated. Alternatively, the non-woven layer may be a separate component, in which case the elastomeric element is attached to the non-woven layer to form the laminate, which is then coupled to the main portion. If one or more layers of the side panel are provided separately, the laminate may be activated either before or after attachment to the main portion. Still further, a zero strain laminate may comprise a stretchable material, such as an extensible or at least partially elastic non-woven material, attached to an elastomeric element. When a stretchable material is used, activation may not be necessary to obtain at least a partially extensible laminate.

Alternatively, each side panel may comprise a pre-stretch laminate including at least an elastomeric element coupled to a layer of non-woven material when the elastomeric element is in a stretched or extended state. The elastomeric element may be subject to an elongation process to place it in the extended state. After attachment to the non-woven layer, the elastomeric element is subsequently relaxed thereby gathering the non-woven layer. As with the zero strain stretch laminate, the non-woven layer of the pre-stretch laminate may be integral with the backsheet, in which case the elastomeric element is activated by stretching, coupled to the desired portions of the back sheet, and relaxed. Alternatively, the non-woven layer may be a separate component, in which case the elastomeric element may be elongated and attached to the non-woven layer either before or after the non-woven layer is coupled to the main portion.

The elastomeric element may be provided as any material and in any form known in the art for providing extensible or elastic side panels. For example, the elastomeric element may be an elastic film, scrim, foam, strands, printed elastomer patterns (such as the patterned elastomers disclosed in U.S. Published Application No. US2004/0193113 to Desai et al. published on Sep. 30, 2004 and entitled "Variable Stretch Composites and Methods of Making the Composite"), or the like. The elastomeric element may also comprise a laminate, such as a separately formed pre-stretch laminate as described above that is applied to a non-woven layer of the outer cover (or other non-woven layer) in a zero-strain manner and subsequently activated.

Any suitable activation processes may be used to form the zero strain or pre-stretch laminate. Mechanical processing, such as advancing the laminate through rollers, engaging teeth, or the like, may be used. Examples of zero strain activation processing and formations of resulting stretchable laminates are described in U.S. Pat. No. 5,167,897 issued to Weber et al. and U.S. Pat. No. 5,156,793 issued to Buell et al.

It will be readily appreciated by those of skill in the art that the overall dimensions of the pull-on article may vary depending on the intended size and age range of the user. For example, it may be desirable to provide pull-on articles of the present invention in a variety of sizes to accommodate various toddler stages of development and to provide such products with features corresponding to one or more of such stages. The size of the side panels may vary and suitable sizes might range from about 2 cm to about 15 cm in length (in the longitudinal direction) and from about 12.7 cm to about 381 cm (measured in the transverse direction).

As best shown with reference to FIG. 6, the article 10 defines side regions encompassing a side panel and adjacent sections of the main portion 12. The exemplary embodiment includes two side regions 100, 102. Side region 100 includes side panel 14 (including front and rear panel portions 70, 74) and transverse regions 104, 106 of the main portion 26. Similarly, side region 102 includes side panel 16 (including front and rear panel portions 72, 76) and transverse regions 108, 110 of the main portion 12.

An informational image 120 is disposed on at least one of the side regions 100, 102 to communicate information relating to the pull-up article 10 to a user. The informational image 120 is selected to communicate information regarding the use of article 10 to a user. The information may relate to a characteristic or feature of the article 10, or may provide instructional or descriptive information regarding the use of article 10.

As used herein, the term "communicate" refers to the ability of the informational image to impress an idea or message upon, or trigger a cognitive response within, a user. As such, communication may rely upon a user's experience or knowledge to arrive at the intended message. Additionally or alternatively, the image preferably illustrates simple concepts that are understood at a basic or visceral level that does not require the prior knowledge or experience of a user. In any event, the image is preferably cognitively functional in that it conveys a message, preferably related to an action or decision to be made, that is generally capable of being understood by a recipient user.

Figure 7:
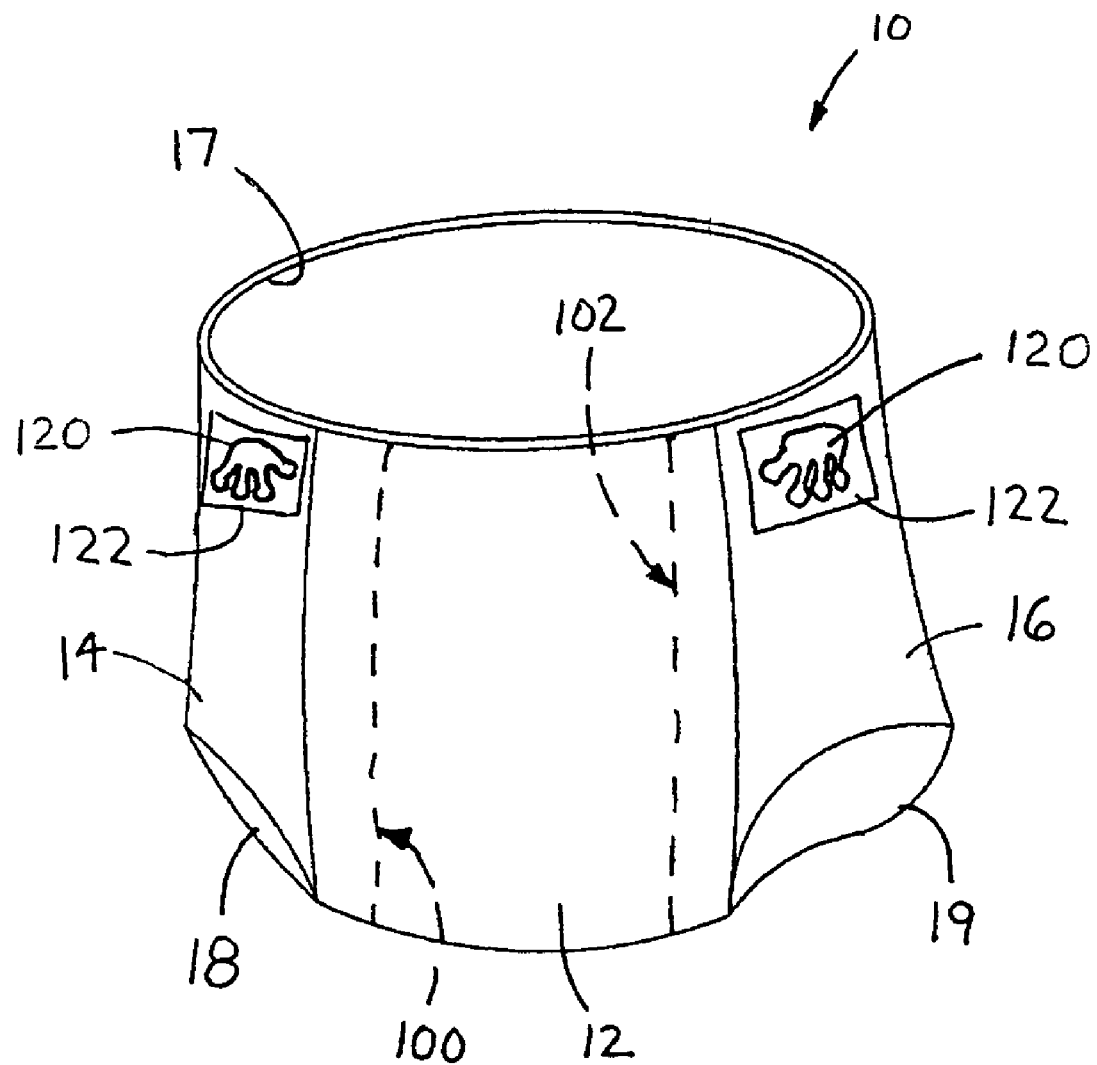
FIG. 7 is a perspective view of an alternative embodiment of a pull-on article having an auxiliary layer with an informational image disposed thereon.

As used herein, the phrase "disposed on" is used to mean that the informational image 120 is applied to, formed on, or otherwise provided with the pull-on article 10. For example, the informational image 120 may be printed directly on the article 10 or an element thereof, or printed on a separate substrate, such as an auxiliary layer of material 122 that is affixed or otherwise joined to the article 10 (either before or after activation), as illustrated in FIG. 7. The auxiliary layer 122 may be formed of non-woven, film, laminate, or other material. The informational image 120 may be applied using any known method, including printing. As used herein, the term "print" includes all printing methods as known in the art, including, but not limited to, digital, ink jet, gravure, screen, and other forms of printing. Regardless of the printing method, the resulting printed image is preferably sufficiently dry and water steadfast to resist transfer in response to dry insults (e.g., abrasion due to contact with outer clothing) and to resist transfer, run, or bleeding in response to contact with liquids (such as water, urine, or drinks).

To provide an image that is legible and comprehensible when the article is positioned about the ankles or knees, the informational image is preferably most visible when the side panels or portions thereof are in a substantially relaxed state. Children may be asked to perform all or a portion of the pull-on article placement. To the extent any assistance is provided, the caregiver will often help only to place a child's feet through the leg openings of the article (i.e., thread the legs through the article). Accordingly, when first confronted with the task of pulling up the article, the article is at the child's ankles or knees. In the ankle, knee, or other position below the hips and buttocks, the side panels are in a relaxed or substantially relaxed state. For example, the side panels rarely exceed 40% extension, are typically at 0-20% extension, and are often at 0-10% extension when the article is positioned below the hips and buttocks. Conversely, once the article is in place about the waist, the child no longer needs to grasp the article and/or apply a pulling force, and thus does not need to view the article or any image disposed thereon, and image legibility and visibility is less important. Therefore, the informational image 120 is preferably readily observable when the side panels are substantially in the relaxed state. Because observation of the image is not needed when the article is in place about the waist, the informational image may be more legible with the side panels in the substantially relaxed state and less legible when the side panels are in a substantially extended state.

With regard to the specific side panel laminates noted above, the informational image is preferably disposed on the side panel with the side panel in the relaxed or substantially relaxed state to maximize legibility of the image in a substantially relaxed state. Examples of informational images that are legible or more legible in the relaxed state are illustrated in FIGS. 15-17.

Figure 15A:
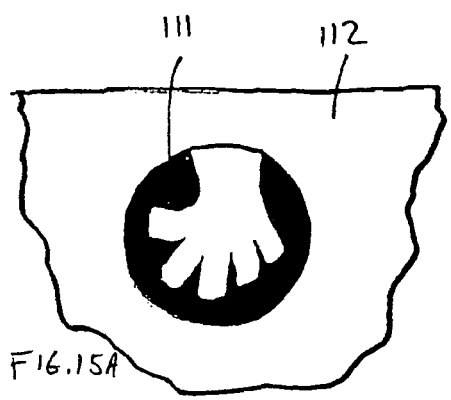
FIGS. 15A and 15B are plan views of an informational image applied to a zero-strain laminate in the relaxed and extended states, respectively.
Figure 15B:
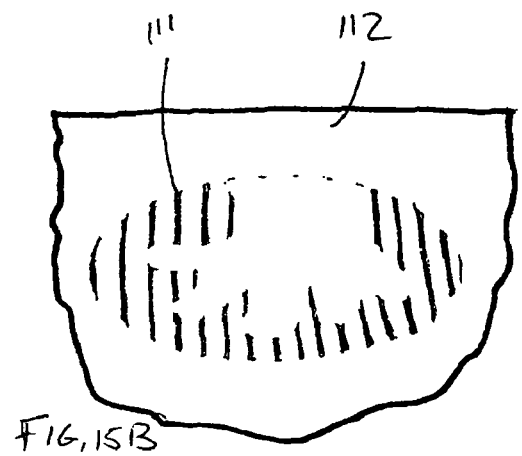

FIGS. 15A and 15B illustrate one example where an image 111 is disposed on an outer layer of non-woven material 112 of a zero stretch laminate in the relaxed and extended states, respectively. The image 111 is distinct, clear, and continuous (and hence legible) when the non-woven layer 112 is in the relaxed state (FIG. 15A). With the non-woven layer 112 stretched in the extended state, discontinuities interrupt the image, making it less legible.

Figure 16A:
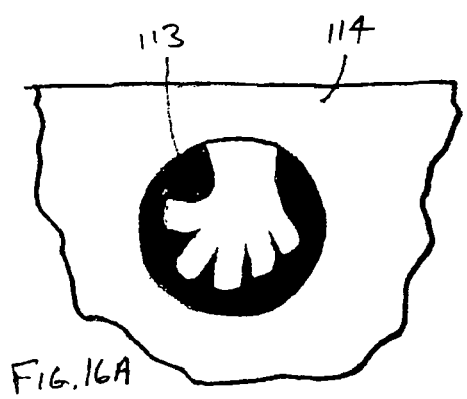
FIGS. 16A and 16B are plan views of an informational image applied to an elastomeric film in the relaxed and extended states, respectively.
Figure 16B:
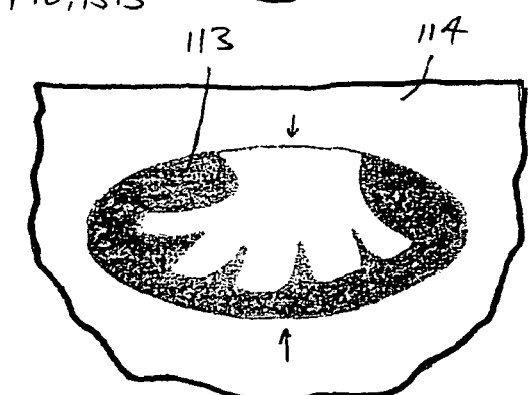

Another example is illustrated in FIGS. 16A and 16B, where an image 113 is shown on an elastomeric film layer 114 in the relaxed and extended states, respectively. When the layer 114 is in the relaxed state (FIG. 16A), the image 113 is more clear and distinct, provides greater contrast with the background color, and is less distorted, thereby providing a legible image. When the layer 114 is in the extended state shown in FIG. 16B, the image 113 has a lighter, less definite, and more distorted appearance.

Figure 17A:
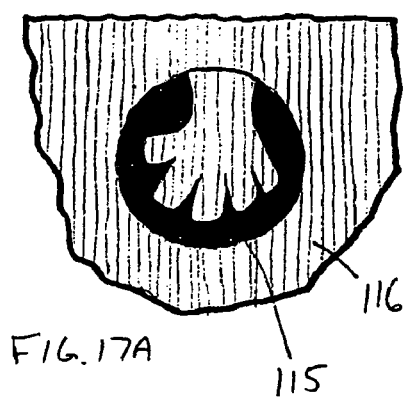
FIGS. 17A and 17B are plan views of an informational image applied to a pre-stretch laminate in the relaxed and extended states, respectively.
Figure 17B:
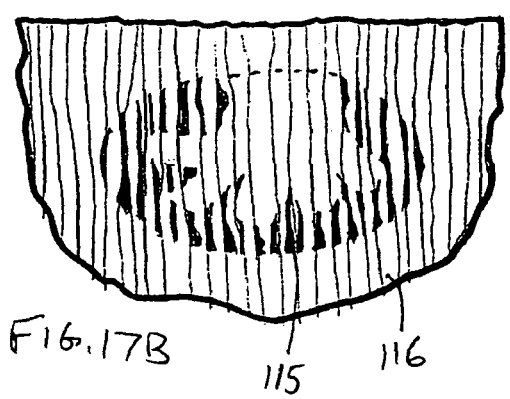

A further example is shown in FIGS. 17A and 17B, which illustrate an image 115 disposed on an outer layer of a pre-stretch laminate 116. With the laminate 116 in the relaxed state (FIG. 17A), the image 115 again is more clear, defined, and continuous, whereas the image 115 is discontinuous and more difficult to comprehend when the laminate is in the extended state illustrated in FIG. 17B.

In each of the foregoing examples, the informational image may be applied with the side panel in either the relaxed state (either before or after activation) or in the extended state. If the side panel is in the relaxed state, the image is applied as an undistorted image that substantially corresponds to the image as it is intended to be viewed by a user, such as the images shown in FIGS. 15A, 16A, and 17A. If the image is applied with the side panel in the extended state, the image is applied as a distorted image, such as those shown in FIGS. 15B, 16B, and 17B, so that the image is undistorted and enhanced when the side panel is subsequently relaxed.

The informational images disclosed herein are particularly suited for pull-on articles intended for use by children. Accordingly, the exemplary images illustrated herein are cognitively functional to a pre-literate child. The informational images preferably use symbols, graphics, or other markings other than words as the primary form of communication, so that a pre-literate child may comprehend and follow the instructions or other information indicated by the image.

As used herein, the terms "pre-literate" and "incapable of reading" are used interchangeably to mean the inability of a child to correctly understand, comprehend and follow prompts written in a language that the child can speak without assistance of a caregiver. The ability of a child to recognize letters and/or read one or two isolated words still means that the child is "incapable of reading" since he or she is unable to understand, comprehend and follow such written prompts, without assistance. However, this definition of "incapable of reading" does not exclude the child from being able to understand, comprehend and follow visual prompts which are presented in the form of drawings, icons, symbols, gestures, cartoons and the like. Furthermore, while the disclosed embodiments are capable of being understood by a pre-literate child, it is not necessary for the images to be understood at this level.

The image may be in the form of any visual representation suitable for communicating information regarding the use of article 10 to a user. Accordingly, the image may include one or more icons, which may comprise, but are not limited to, pictorial symbols, photographs, drawings, cartoons, and logos. For example, the icons may be provided as drawings of a child or an anthropomorphic image of an animal using the pull-on article 10. Similarly, the icons may include well-known cartoon characters or brand logos, or characters specifically created to be associated with the article. The icons may further include symbols, such as arrows, to indicate motion, movement, or directionality.

The informational image may be arranged in any manner as long as it communicates the desired information to a user. The image may be a single icon or a series of icons. If a series of icons is provided, each icon may be the same or different. Different icons may be complementary to one another, in that they are related to the same concept or activity (such as open and closed hands), or incorporate a common visual element (such as a similar appearance, color, or theme). The icons may be arranged in any suitable fashion, such as, but not limited to, vertically, horizontally, diagonally, circular, arcs, and combinations thereof.

The informational image may optionally include a character graphic that can increase a user's interest in the product. The term "character graphic" is used herein to refer to a graphic containing an anthropomorphic image, and in particular an image having or suggesting human form or appearance which ascribes human motivations, characteristics or behavior to inanimate objects, animals, natural phenomena, toys, cartoon characters, or the like. The character graphic may be associated with popular characters in the media, advertising or well known in a particular culture. Ideally they are characters that the user, particularly if a child, cares about and want to identify with.

In the illustrated embodiments, the informational image 120 communicates a location in which to grip the article 10 as it is pulled into place on a user. In an article having extensible side panels, forces are more effectively transferred from radial side locations to the front and back regions than from the front of the article. Accordingly, the informational image 120 is located in a side region 100 or 102 of the article 102, which include these radial side locations. It is preferable to pull the diaper at both side regions, and therefore informational images 120 may be provided in both side regions, as illustrated in FIG. 1. Furthermore, it is preferable to grip the article near an upper edge, and therefore the images 120 may be positioned in an upper portion of each side panel. While the images may be different, they are preferably substantially similar. As used herein, "substantially similar images" include identical images, mirror images, images incorporating common visual elements, the same or similar image shapes having different colors, inverted foreground and background images (i.e., the same or similar image in positive and negative), the same or similar image in both solid and outline, and the like.

In an exemplary embodiment of a cognitively functional graphic, the informational image 120 is provided as a hand graphic to communicate to a user that the article is to be grasped in the location of the image. As used herein, the phrase "hand graphic" refers to an image formed to resemble a hand, a hand with a portion of an arm or body, or one or more portions thereof, such as a palm, one or more fingers, one or more fingertips, and the like. The hand may resemble a human, animal, anthropomorphic, cartoon character, mythical creature, or other style. Furthermore, the hand image is not limited to including five fingers (i.e., four fingers and a thumb). When intended for use by children, the image 120 may have any size, but is preferably sized to generally correspond to the size of a child's hand or a portion thereof. Accordingly, the image preferably has a lateral dimension of approximately 1 to approximately 10 centimeters and a longitudinal dimension of approximately 1 to approximately 5 centimeters. In an exemplary embodiment, the image may have a lateral dimension of approximately 6 centimeters and a longitudinal dimension of approximately 3 centimeters.

Graphics other than the image of a hand may be used to attract a user's attention and indicate a gripping location. When the article is intended for use by a child, it may carry images of a cookie or other foods, a spoon, a doorknob, a handle, or other object commonly grasped by a child. Alternatively, the indicia may include images of stars, balloons, or other items easily recognized by a child, or patterns and decorative designs that would attract a child's attention.

Figure 8:
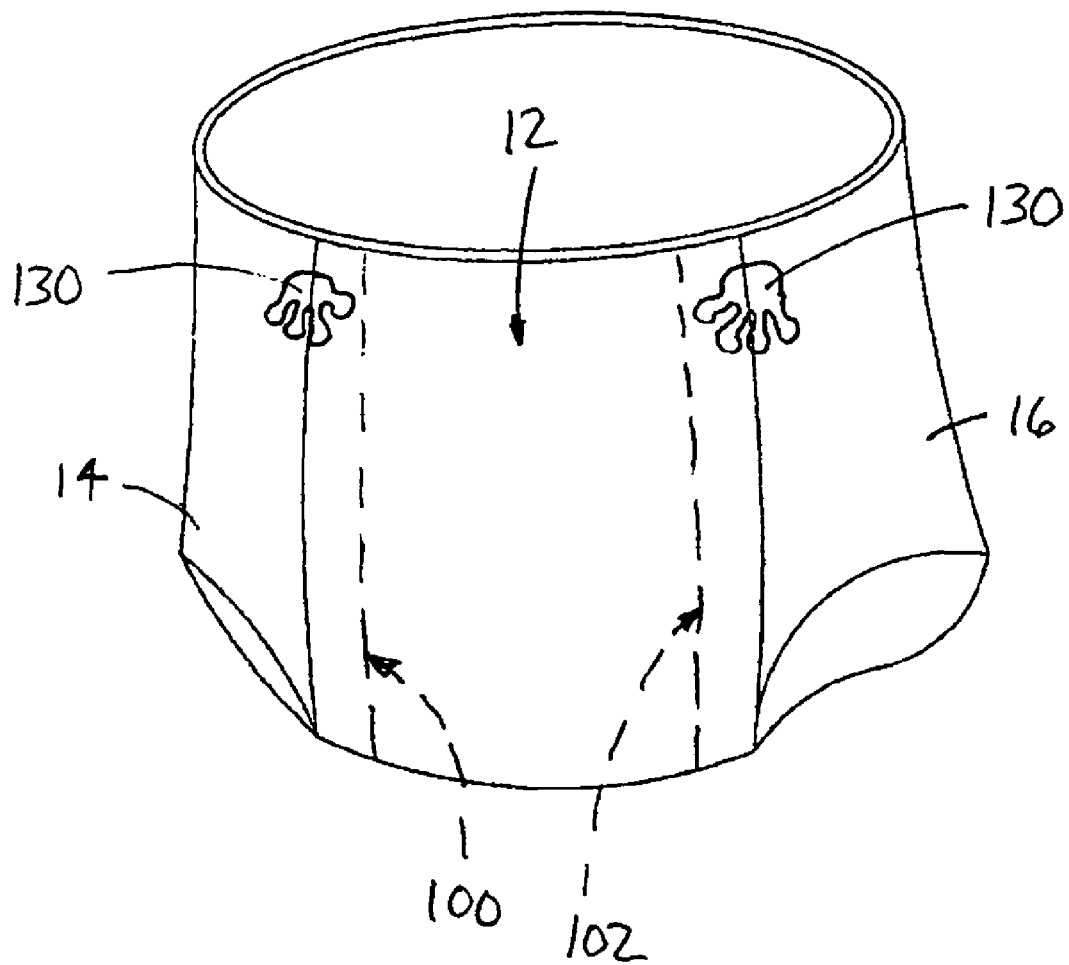
FIG. 8 is a perspective view of a pull-on article similar to that of FIG. 1 showing an alternative informational image location.

While the informational images 120 illustrated in FIG. 1 are positioned entirely within a respective side panel, the images may be located at other positions within the side regions 100, 102. For example, part of the image may be located on a side panel while another part may be located on an adjacent transverse region of the main portion, as with informational image 130 illustrated in FIG. 8. While image 130 is shown positioned near a front waist region, it will be appreciated that the image 130 may be similarly positioned near the rear waist region.

Figure 9:
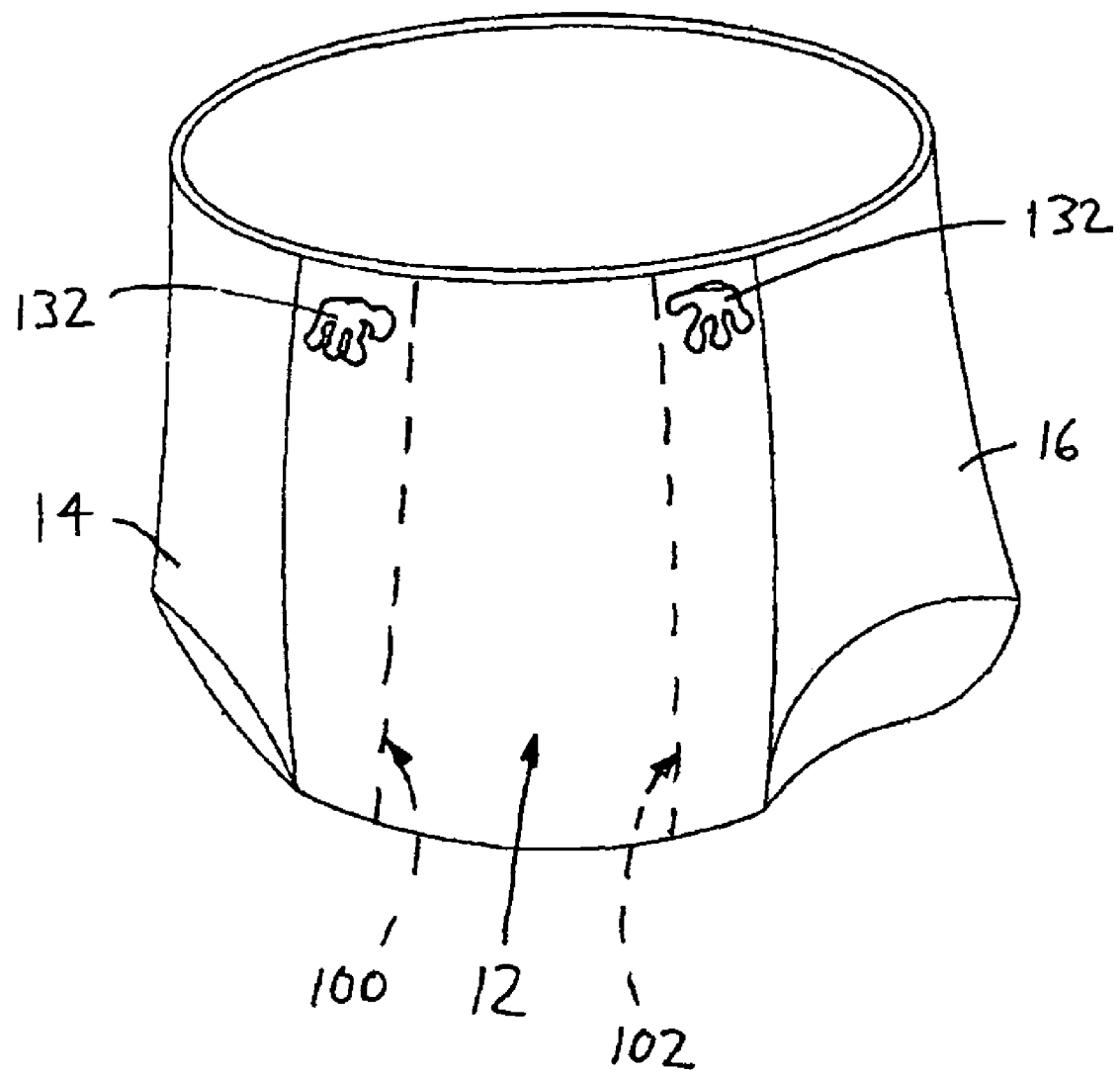
FIG. 9 is a perspective view of a pull-on article similar to that of FIG. 1 showing an alternative informational image location.

In addition, the image may be located entirely within a front or rear transverse region of the main portion, as with information image 132 illustrated in FIG. 9. The transverse regions are located adjacent to the side panels so that, when an image is provided entirely within a transverse region, it still indicates a more desirable pulling location than the center of the main portion. While a continuous, unitary side panel is illustrated in FIG. 1, the side panel may be formed of separate panel portions as illustrated in FIGS. 4-6. Accordingly, the image may be located entirely within a particular side panel portion, span adjacent joined side panel portions, or span a side panel portion and a transverse region of the main portion.

Figure 18:
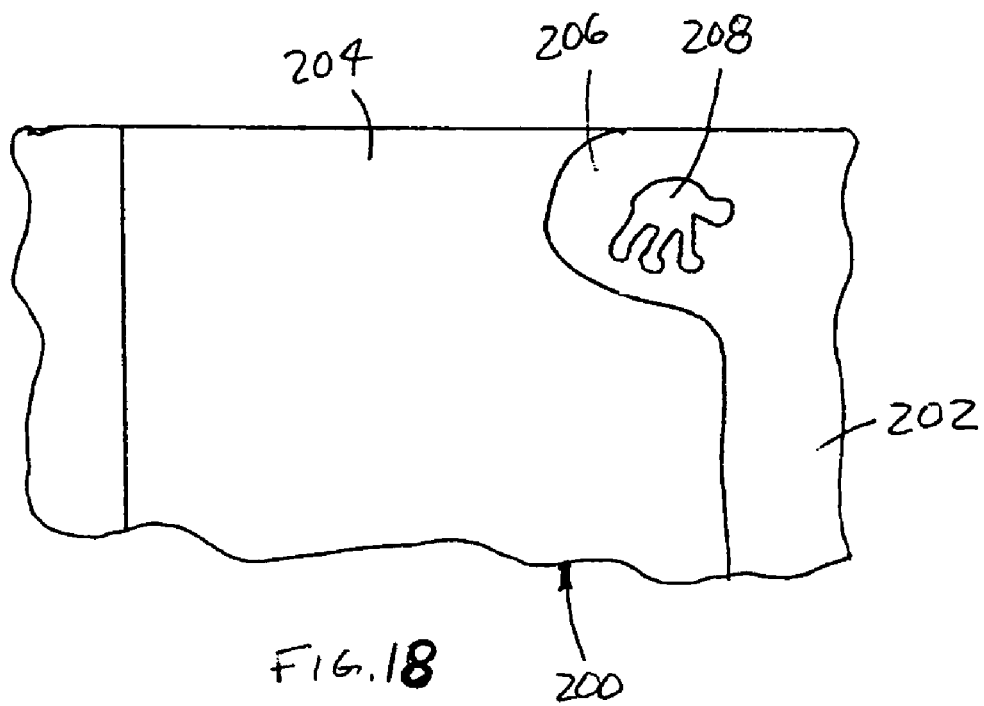
FIG. 18 is an enlarged plan view of part of an article having a main portion with a projection on which the informational image is disposed.
Figure 19:
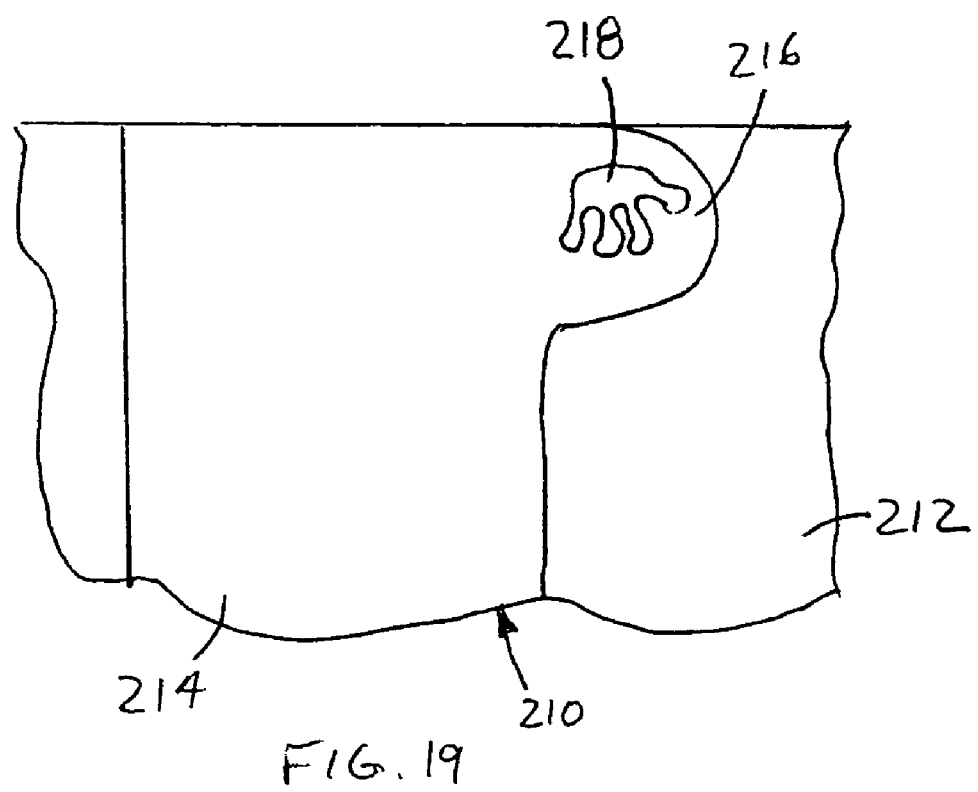
FIG. 19 is an enlarged plan view of part of an article having a side panel with a projection on which the informational image is disposed.

The side panel or the main portion may include a projection, such as a lateral projection, on which at least a portion of the informational image is disposed. As illustrated in FIG. 18, an article 200 includes a main portion 202 and a side panel 204. The main portion 202 includes a projection 206 extending into the side panel area. An informational image 208 is disposed on at least a portion of the projection 206. The main portion 202 may comprise a plurality of layers of material, and the projection 206 may comprise one or more of those layers. For example, the main portion 202 may comprise a film layer that forms the projection 206. In the alternative embodiment illustrated in FIG. 19, an article 210 includes a main portion 212 and a side panel 214. The side panel 214 includes a projection 216 extending into the transverse region of the main portion 212, and an informational image 218 is disposed on at least a portion of the projection 216. The side panel 214 may comprise a plurality of material layers, and the projection 216 may comprise one or more of those layers.

Figure 10:
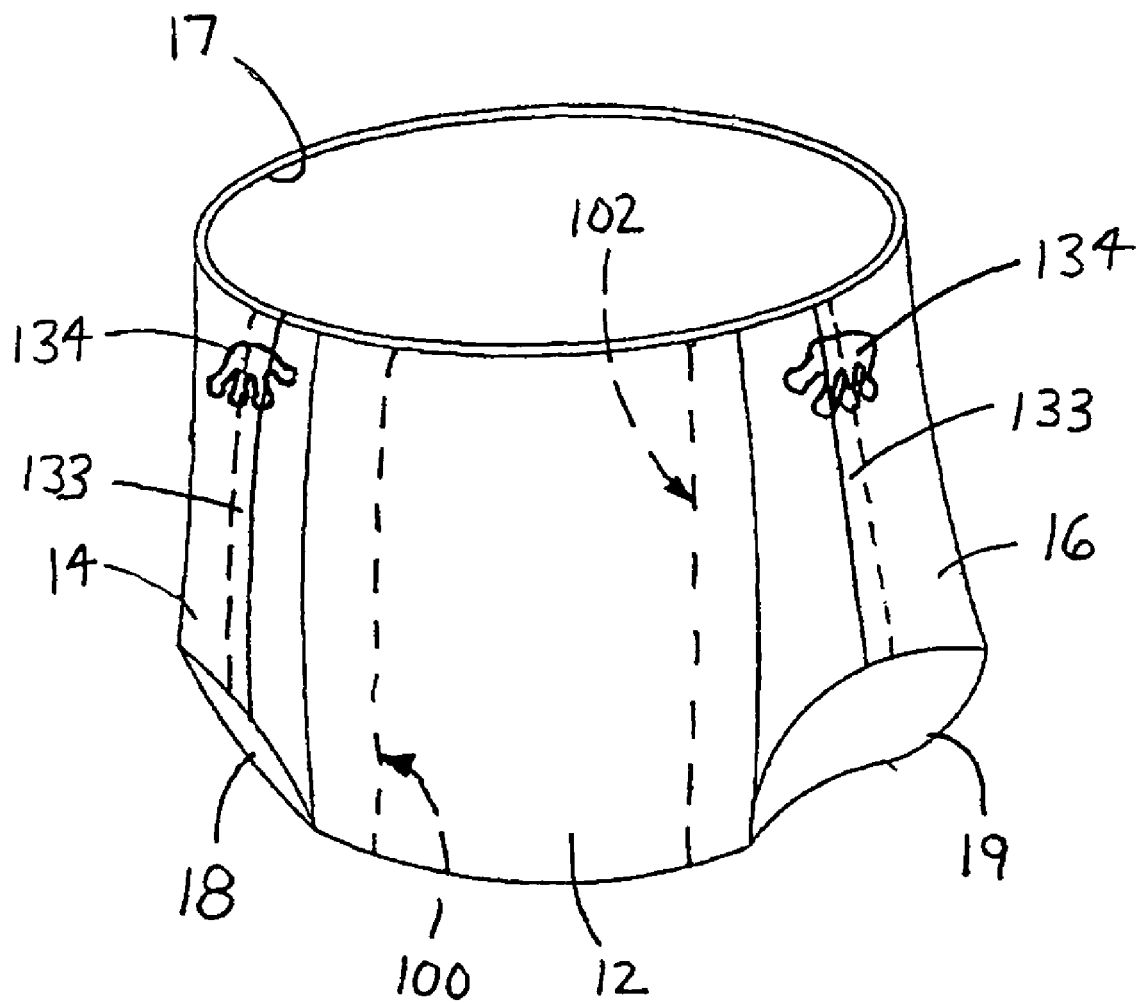
FIG. 10 is a perspective view of a pull-on article similar to that of FIG. 1 showing an alternative informational image location.

Whether the side panel is unitary or formed of separate panel portions, seams may be formed over which the image may be applied. Seams are formed when adjacent edges of material are bonded together over at least a portion of the adjacent edges of material to permanently join the materials. The attachment of the panel portions is permanent in the sense that the panel portions are intended to maintain a joined relationship prior to and during use. The panel portions may, however, be frangible or frangibly connected to facilitate removal and/or disposal of the article. In an article having unitary side panels, seams may be formed where the side panel joins the front and rear waist regions. Similarly, a seam may be formed between separate side panel portions that are joined together. The informational image may be formed over any seam formed in the side regions. For example, the panel portions may be joined to form a seam 133, and the image may span the seam, as illustrated in FIG. 10 by informational item 134.

Figure 20:
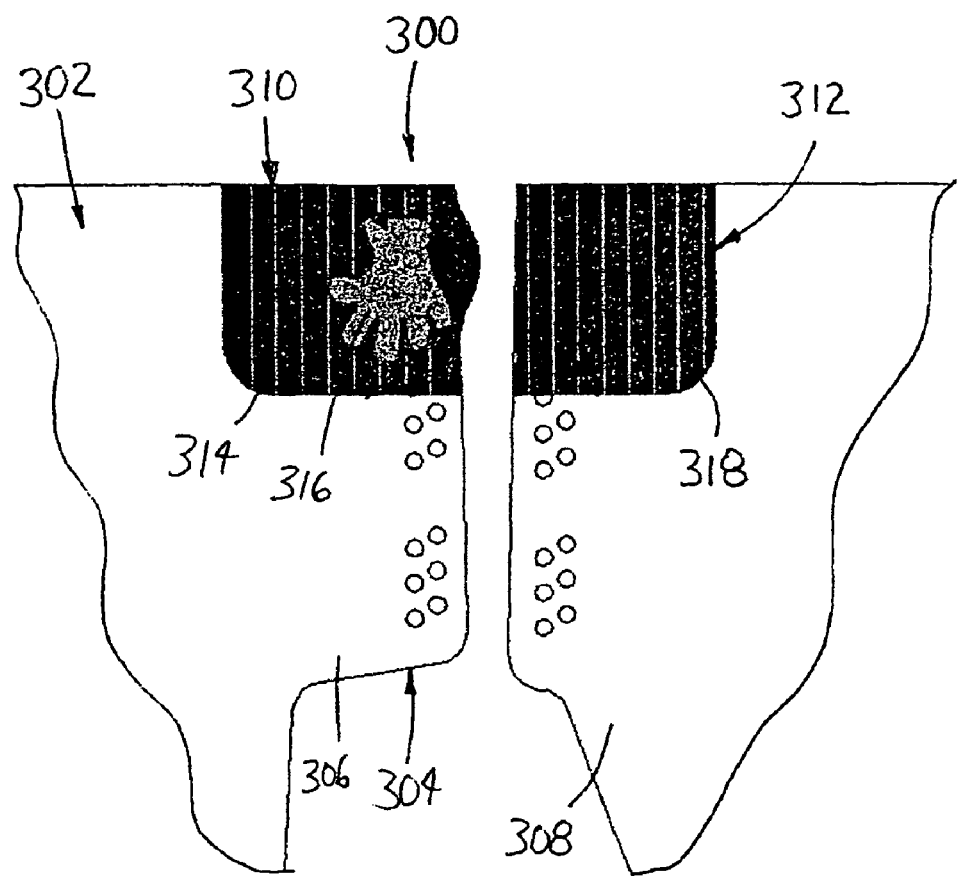
FIG. 20 is an enlarged plan view of part of an article having an informational image spanning a seam of a side panel.

FIG. 20 illustrates an informational image 300 spanning a seam of an article 302. The article 302 includes a side panel 304 including a front panel portion 306 and a rear panel portion 308. The front and rear panel portions 306, 308 may be joined, such as by bonding, to form a seam, however FIG. 20 shows the panel portions prior to being joined. The informational image 300 is disposed on the side panel 304 and includes a front image portion 310 and a rear image portion 312. In the illustrated embodiment, the front image portion 310 includes a background graphic 314 and a hand graphic 316, while the rear image portion includes a background graphic 318. When joined together, a peripheral region of the front panel portion 306 overlies a peripheral region of the rear panel portion. In this embodiment, the hand graphic 316 is disposed entirely on the front panel portion 306, so that the subsequently formed seam does not disrupt the image. The hand graphic 316 may, alternatively, be positioned entirely on the rear panel portion 308, or may have portions disposed on both the front and rear panel portions 306, 308.

Figure 21:
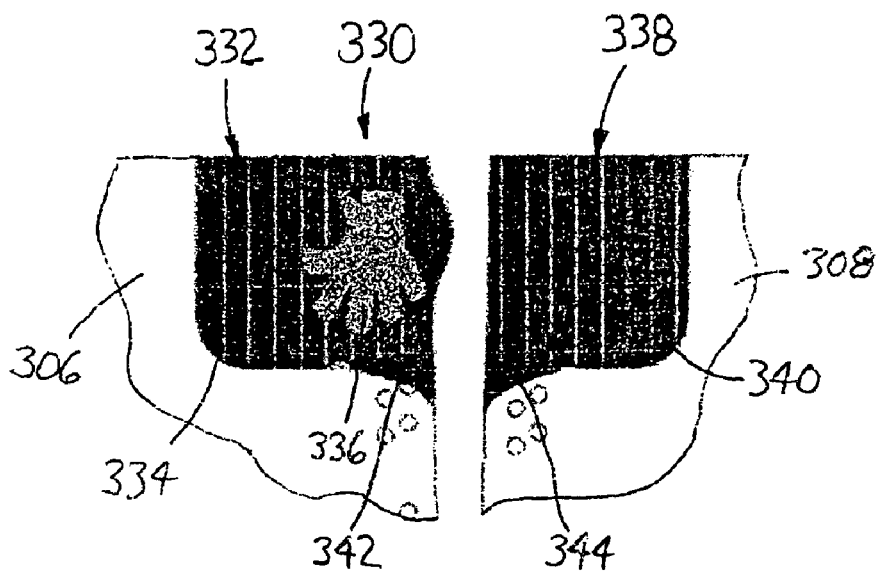
FIG. 21 is an enlarged plan view of an alternative informational image spanning a seam of a side panel.

FIG. 21 illustrates an informational image 330 similar to that shown in FIG. 20, but with a slight variation. Specifically, the informational image 330 includes a front image portion 332 including a background graphic 334 and a hand graphic 336 and a rear image portion 338 including a background graphic 340. The background graphics 334, 340 include curved or contoured lower borders 342, 344 near the lateral edges of the front and rear panel portions 306, 308. Since the image portions 332, 334 may be applied with the article in a flat configuration prior to joining the side panel portions 306, 308, there is a possibility that the image portions 332, 334 may not precisely align with one another. The curved lower borders 342, 344 make any such misalignment less readily visible, thereby allowing for greater tolerances for longitudinal tracking between side panel portions.

Figure 11:
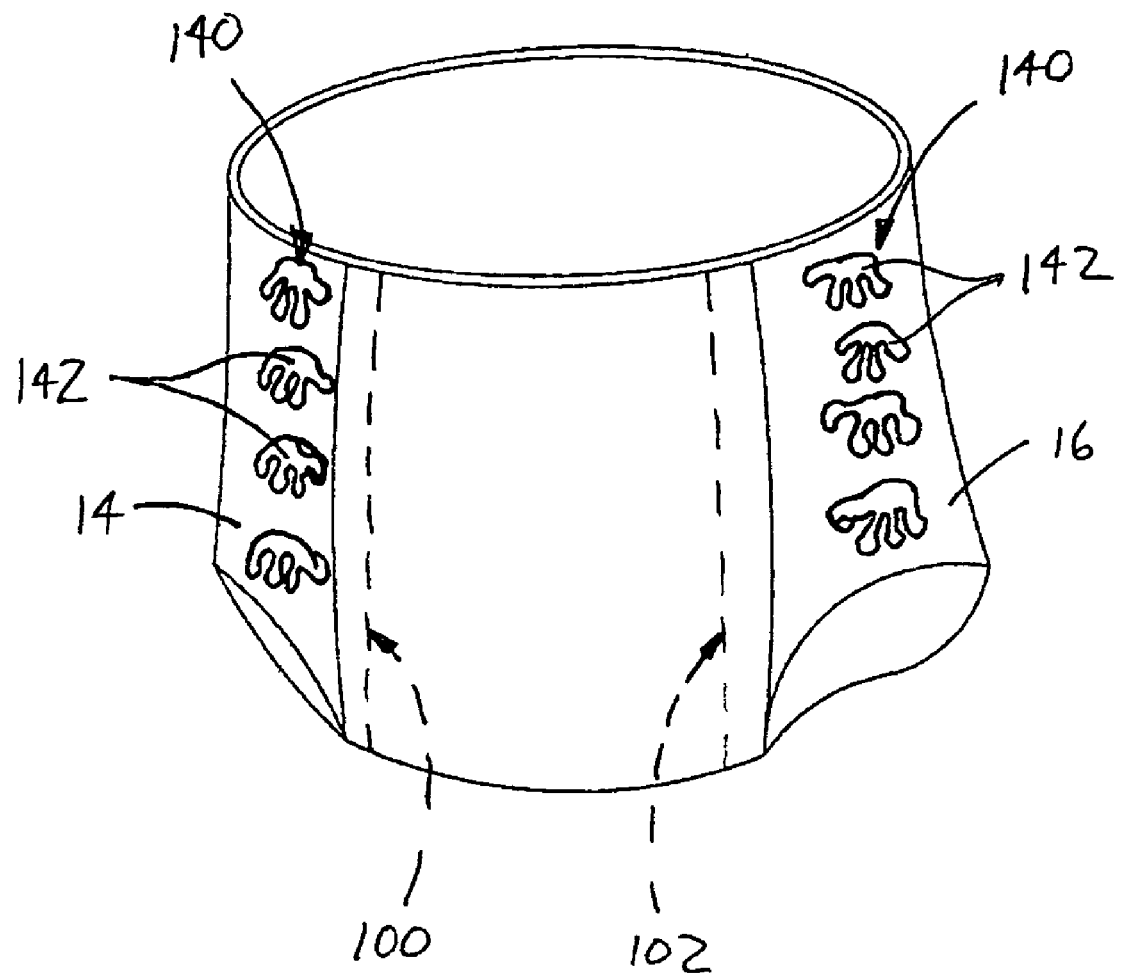
FIG. 11 is a perspective view of a pull-on article similar to that of FIG. 1 showing an alternative informational image comprising a plurality of icons.

Rather than a single icon, the image may include a plurality or series of icons in one or more of the side regions 14, 16. As illustrated in FIG. 11, for example, each side panel defines an upper edge and a lower edge with a longitudinal length extending from the upper edge to the lower edge. The informational image 140 extends substantially across the longitudinal length of the side panel. In the exemplary embodiment, the informational image 140 includes a repeating pattern of hand icons 142. Whether a single or multiple icons are provided, the image is preferably registered so that it is located in substantially the same location on each article, however non-registered images are suitable in certain alternate embodiments.

The informational image 120 is preferably viewable from an exterior of the article, and therefore the informational image is preferably disposed on an outer or garment-facing layer of the article or an element thereof. In most cases, the image is disposed on an exterior layer of the article, such as the outer surface of the backsheet, or an auxiliary layer that is coupled to an exterior layer of the article. Alternatively, the informational image may be disposed on an interior layer and is viewable through one or more transparent or translucent outer layers. In certain alternate embodiments, the image may be viewable from the interior of the article to allow the child to identify the target grasping location if the interior surface is exposed while the article is at the child's ankles or knees. In this case, the image may be printed on an interior surface or on a layer that is visible from an interior of the article. Accordingly, the informational image may be disposed such that is viewable from an exterior only, from both an exterior and an interior, or from an interior only of the article.

In accordance with additional aspects of this disclosure, a pull-on wearable article may be provided having an informational image incorporating a texture feature. The texture feature is positioned sufficiently proximate the informational image so that the texture feature is associated with the informational image, thereby to form a composite image. As used herein, the term "proximate" includes locations positioned both adjacent to or at least partially coincident with one another.

The texture feature imparts a unique visual appearance to the image, such as by forming layers, regions of relative smoothness or roughness, varying reflectivity, color enhancements, or other visual effect. The texture feature may increase the legibility of the image in poor lighting conditions or at viewing angles deviating significantly from the perpendicular. Additionally or alternatively, the texture feature may enhance at least a portion of the informational image or may form a separate portion of the informational image. For example, the informational image may form a part of a hand image, such as a palm, while the texture feature forms another part of the hand image, such as fingers or finger pads, so that the combination of the informational image and the texture feature form a composite image. Alternatively, the informational image may form a complete hand image while the texture feature is applied to part or the entire hand image to form the composite image. The combination of the informational image and texture feature may be provided on any known type of pull-on wearable article having extensible side panels, without regard to the type, or method of construction of the side panels, and regardless of the state (i.e., extended or relaxed) in which the informational image is more legible, if any.

Figure 12:
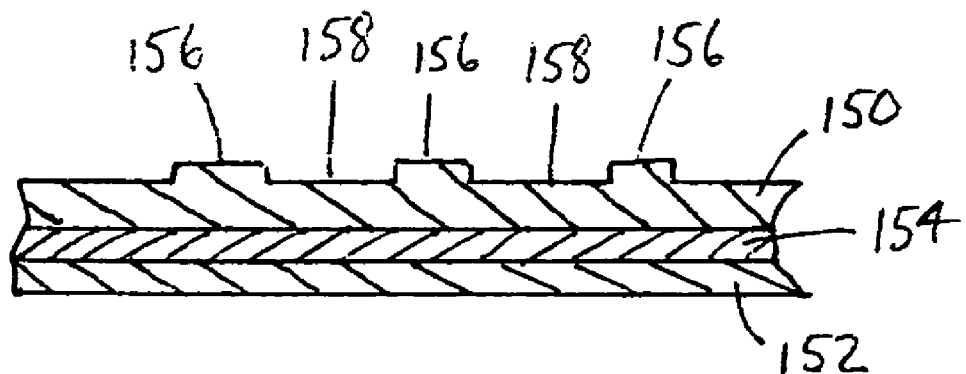
FIG. 12 is a side elevational view, in cross-section, of an article having a texture feature on an exterior surface.

In one exemplary embodiment, the texture feature may include localized projections formed in an outer surface of the article. FIG. 12 illustrates a cross-sectional view of a portion of an article carrying an informational image. The article at this portion includes an outer layer 150 of non-woven material, an inner layer 152 of non-woven material, and an elastomeric element 154 disposed between the outer and inner layers 150, 152. The outer layer 150 is formed with localized projections 156 defining recesses 158 therebetween. The projections 156 may be formed by embossing or other processes that raise portions of at least the outer layer.

Figure 13:
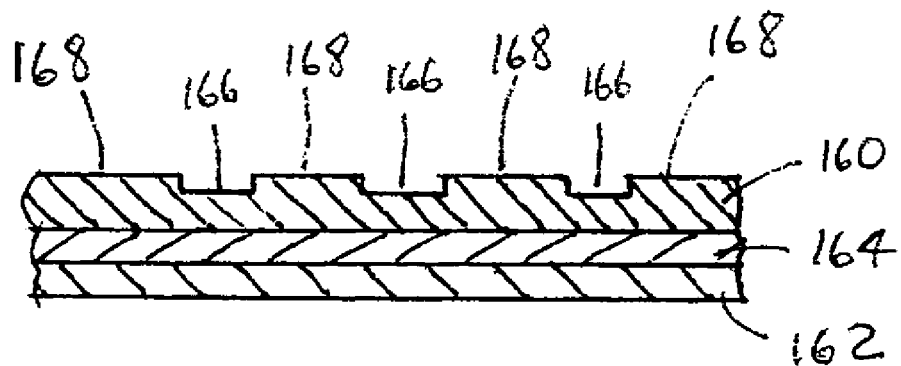
FIG. 13 is a side elevational view, in cross-section, of an article having an alternative embodiment of a texture feature on an exterior surface.

In an alternative embodiment, the texture feature may include localized recesses formed in the outer surface of the article. FIG. 13 illustrates a cross-sectional view of a portion of an article having an outer layer 160 of non-woven material, an inner layer 162 of non-woven material, and an elastomeric element 164 disposed between the outer and inner layers 160, 162. The outer layer 160 is formed with localized recesses 166 defining projections 168 therebetween. The recesses may be formed in any known manner, including application of a bond pattern between the outer layer 160 and either the inner layer 162 or elastomeric element 164. The bond pattern secures discrete locations of the outer layer 160 to one of the other interior layers to form an associated recess 166.

Figure 14:
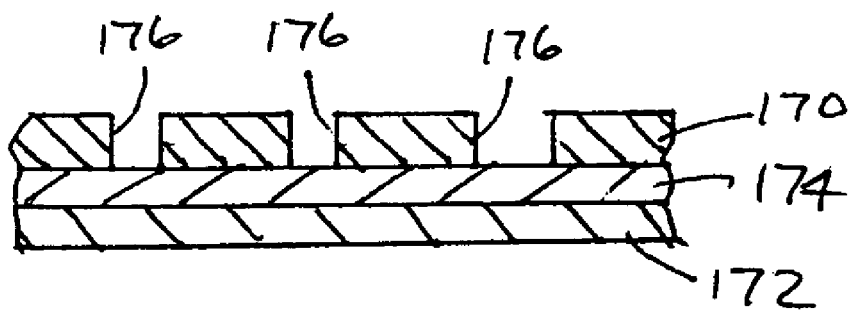
FIG. 14 is a side elevational view, in cross-section, of an article having an alternative embodiment of a texture feature on an exterior surface.

In a further exemplary embodiment, the texture feature may be formed by adjacent layers of material. As illustrated in FIG. 14, a portion of a pull-on article includes an outer layer 170 of non-woven material, an inner layer 172 of non-woven material, and an elastomeric element 174 disposed between the outer and inner layers 170, 172. The outer layer 170 is formed with slits, slots, holes, or other regular or irregular apertures or openings 176 to expose portions of the elastomeric element 174. Accordingly, it will be appreciated that the exterior surface of the article, at least in this location, is formed by both the outer layer 170 and the exposed portions of the elastomeric layer 174. The outer layer 170 has a thickness sufficient to create a varying exterior surface appearance.

While the exemplary embodiments of texture features disclosed herein identified specific layers and types of material, it will be appreciated that other combinations and types of material layers may be used. Furthermore, while specific processes for forming the texture feature are suggested, any type of known process for forming the features may be used. While the texture feature is preferably formed by a mechanical treatment (such as embossing, ring-rolling, bonding, scoring, puncturing, or slitting), it may also be formed by non-mechanical treatments such as laser, hot air, chemical, or other processes.

Each of the mechanical treatments may result in particular types of texture effects. Embossing may be performed either hot or cold, with either a smooth or a patterned roll, and may result in projections, recesses, areas of relative smoothness, areas of compression (and associated compression resistance), or combinations thereof. Ringrolling may result in openings, projections, recesses, or combinations thereof. Methods for forming structural elastic-like film (SELF) may be employed, such as those disclosed in U.S. Pat. No. 5,554,143 issued to Roe et al. on Sep. 10, 1996 entitled "Absorbent Article with Multiple Zone Structural Elastic-Like Film Web Extensible Waist Feature" and U.S. Pat. No. 5,518,801 issued to Chappell et al. on May 21, 1996 entitled "Web Materials Exhibiting Elastic-Like Behavior", and may result in projections, recesses, or combinations thereof. Scoring may cause surface morphology such as areas of relative roughness or fuzziness. Puncturing may cause openings at least partially surrounded by three-dimensional projections.

The texture effect may further be influenced or at least partially formed by the elastomeric layer. For example, an elastomeric element having a discontinuous surface, such as the vacuum formed elastomer disclosed in U.S. Published Application No. US2003/0120240 to Buell et al. published on Jun. 26, 2003 and entitled "Disposable Pant-Type Diaper Having Improved Protection Against Red Marking" may be provided against which the outer cover at least partially conforms, to form a layered outer surface.

Still further, the texture feature may be formed by locally contracting discrete regions of the article. This may be accomplished by a mechanical process or by another process such as heat shrinking.

While the foregoing illustrated embodiments describe the informational image as conveying a location in which to grasp and pull the article, it will be appreciated that the image may include a cognitively functional graphic that conveys any instructional, informational, or other message to a user. In addition or as an alternative to assisting in pulling up or down the article, the informational image may communicate information regarding opening or closing refastenable side panels, folding and/or handling of used diapers during disposal, or other instructions. The informational image may also communicate characteristics or properties of the article, such as gender appropriateness, suitability for toilet training, or other training specific information (e.g. indicating incorporation of a feel wet liner). Still further, the informational image may communicate information about the user, such as growth (by conveying changes in size of the article). An informational image including a cognitively functional graphic may be provided on any known type of pull-on wearable article having extensible side panels, without regard to the state of the side panels (i.e., extended or relaxed) in which the informational image is more visible, if any.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pull-on wearable article comprising:
   a main portion including an outer cover, the main portion defining a front waist region having first and second longitudinal side edges, a rear waist region having first and second longitudinal side edges, and a crotch region extending between and connecting the front and rear waist regions;
   a first extendable side panel extending between and connecting the first longitudinal side edge of the front waist region and the first longitudinal side edge of the rear waist region and a second extendable side panel extending between and connecting the second longitudinal side edge of the front waist region and the second longitudinal edge of the rear waist region to form the article in a closed waist configuration, at least a portion of each side panel being extendable between a relaxed state and an extended state; and
   an informational image disposed entirely in the first side panel or the second side panel, wherein the informational image is legible when the first and second side panels are substantially in the relaxed state.

2. The pull-on wearable article of claim 1, in which the informational image is more legible with the side panels in the substantially relaxed state and less visible when the side panels are in a substantially extended state.

3. The pull-on wearable article of claim 1, in which the informational image comprises a cognitively functional graphic.

4. The pull-on wearable article of claim 1, in which the informational image communicates a pulling location in which to grip the article.

5. The pull-on wearable article of claim 4, in which the informational image comprises a hand graphic.

6. The pull-on wearable article of claim 5, in which the hand graphic has size dimensions substantially corresponding to at least a portion of a child's hand.

7. The pull-on wearable article of claim 6, in which the hand graphic has a lateral size dimension of approximately 1 to approximately 10 centimeters and a longitudinal size dimension of approximately 1 to approximately 5 centimeters.

8. The pull-on wearable article of claim 1, in which each side panel includes an upper edge and a lower edge, and in which the informational image is located nearer the upper edge of the side panel.

9. The pull-on wearable article of claim 1, in which each side panel has an upper edge and a lower edge and defines a longitudinal length extending from the upper edge to the lower edge, and in which the informational image extends substantially across the longitudinal length of the first side panel.

10. The pull-on wearable article of claim 9, in which the informational image comprises a plurality of icons.

11. The pull-on wearable article of claim 1, further comprising a second informational image disposed in the second side panel.

12. The pull-on wearable article of claim 11, in which the first informational image is substantially similar to the second informational image.

13. The pull-on wearable article of claim 1, in which the informational image is located partially in one of the side panels and partially in one of the transverse portions bordering that side panel.

14. The pull-on wearable article of claim 1, in which each side panel comprises a front panel portion associated with a respective main portion front waist region and a rear panel portion associated with a respective main portion rear waist region, each front and rear panel portions being joined at a seam.

15. The pull-on wearable article of claim 14, in which at least a portion of the informational image is located on the seam.

16. The pull-on wearable article of claim 1, in which at least one side panel is releasably coupled to the main portion front waist region or the main portion rear waist region.

17. The pull-on wearable article of claim 1, in which at least one side panel comprises first and second side panel portions, and in which the first side panel portion is releasably fastenable to the second side panel portion.

18. The pull-on wearable article of claim 1, in which each side panel comprises a separate side panel sheet coupled to the main portion.

19. The pull-on wearable article of claim 1, in which each side panel comprises a portion of the outer cover.

20. The pull-on wearable article of claim 1, in which each side panel comprises a layer of non-woven material and an elastomeric element.

21. The pull-on wearable article of claim 20, in which the elastomeric element comprises an elastomeric film.

22. The pull-on wearable article of claim 20, in which the elastomeric element comprises elastomeric strands.

23. The pull-on wearable article of claim 20, in which the informational image is disposed on an exterior surface of the article.

24. The pull-on wearable article of claim 23, in which the exterior surface comprises the elastomeric element.

25. The pull-on wearable article of claim 23, in which the exterior surface comprises the layer of non-woven material.

26. The pull-on wearable article of claim 20, in which the informational image is disposed on an interior layer having an exterior surface visible through at least a portion of an exterior layer of the article.

27. The pull-on wearable article of claim 20, in which the informational image is associated with the side region with the elastomeric element in a relaxed state.

28. The pull-on wearable article of claim 20, in which the informational image comprises a distorted informational image, and in which the distorted informational image is associated with the side region with the elastomeric element in an extended state.

29. The pull-on wearable article of claim 20, in which each side panel comprises a zero strain stretch laminate.

30. The pull-on wearable article of claim 20, in which each side panel comprises a pre-stretch laminate.

31. The pull-on wearable article of claim 1, in which the informational image is formed on an auxiliary substrate, and in which the auxiliary substrate is coupled to the article in the side region.

32. The pull-on wearable article of claim 31, in which the auxiliary substrate comprises at least one material selected from a group of materials comprising non-woven, film, and laminate materials.

33. The pull-on wearable article of claim 1, in which the informational image comprises a printed image.

34. The pull-on wearable article of claim 1, in which the main portion further includes a liquid permeable topsheet and an absorbent core disposed between the outer cover and the topsheet to form an absorbent wearable article.

35. The pull-on wearable article of claim 1, further comprising a texture feature positioned proximate to the informational image to form a composite image.

36. A pull-on wearable article comprising:
- a main portion including an outer cover, the main portion defining a front waist region having first and second longitudinal side edges, a rear waist region having first and second longitudinal side edges, and a crotch region extending between and connecting the front and rear waist regions;
- a first extendable side panel extending between and connecting the first longitudinal side edge of the front waist region and the first longitudinal side edge of the rear waist region and a second extendable side panel extending between and connecting the second longitudinal side edge of the front waist region and the second longitudinal edge of the rear waist region to form the article in a closed waist configuration, at least a portion of each side panel being extendable between a relaxed state and an extended state, each side panel including a front panel portion associated with a respective main portion front waist region and a rear panel portion associated with a respective main portion rear waist region; and
- an informational image disposed entirely in the first side panel or the second side panel, wherein the informational image is legible when the first and second side panels are substantially in the relaxed state.

37. The pull-on wearable article of claim 36, in which the informational image is more legible with the side panels in the substantially relaxed state and less visible when the side panels are in a substantially extended state.

38. The pull-on wearable article of claim 36, in which the informational image comprises a cognitively functional graphic.

39. The pull-on wearable article of claim 36, in which the informational image communicates a pulling location in which to grip the article.

40. The pull-on wearable article of claim 39, in which the informational image comprises a hand graphic.

41. The pull-on wearable article of claim 40, in which the hand graphic has size dimensions substantially corresponding to at least a portion of a child's hand.

42. The pull-on wearable article of claim 41, in which the hand graphic has a lateral size dimension of approximately 1 to approximately 10 centimeters and a longitudinal size dimension of approximately 1 to approximately 5 centimeters.

43. The pull-on wearable article of claim 36, in which each respective pair of front and rear panel portions is joined at a seam.

44. The pull-on wearable article of claim 36, in which the front panel portion is releasably fastenable to the respective rear panel portion of each respective pair of front and rear panel portions.

45. The pull-on wearable article of claim 36, in which each side panel comprises a separate side panel sheet coupled to the main portion.

46. The pull-on wearable article of claim 36, in which each side panel comprises a portion of the outer cover.

47. The pull-on wearable article of claim 36, in which each side panel comprises a zero strain stretch laminate.

48. The pull-on wearable article of claim 36, in which each side panel comprises a pre-stretch laminate.

49. The pull-on wearable article of claim 36, in which the informational image is formed on an auxiliary substrate, and in which the auxiliary substrate is coupled to the article in the side region.

50. The pull-on wearable article of claim 36, in which the informational image comprises a printed image.

51. The pull-on wearable article of claim 36, in which the main portion further includes a liquid permeable topsheet and an absorbent core disposed between the outer cover and the topsheet to form an absorbent wearable article.

52. The pull-on wearable article of claim 36, further comprising a texture feature positioned proximate to the informational image to form a composite image.

* * * * *